United States Patent [19]
Bodor

[11] Patent Number: 4,479,932
[45] Date of Patent: Oct. 30, 1984

[54] BRAIN-SPECIFIC DRUG DELIVERY
[75] Inventor: Nicholas S. Bodor, Gainesville, Fla.
[73] Assignee: University of Florida, Gainesville, Fla.
[21] Appl. No.: 379,316
[22] Filed: May 18, 1982
[51] Int. Cl.³ .......................... A61K 49/00; C07J 1/00
[52] U.S. Cl. ..................................... 424/9; 260/397.4; 546/316; 564/381; 564/382
[58] Field of Search .................. 424/1, 1.5, 9; 260/397.4; 546/316; 564/381, 382

[56] References Cited
U.S. PATENT DOCUMENTS

| | | | |
|---|---|---|---|
| 4,035,507 | 7/1977 | Bodor et al. | 424/319 |
| 4,065,566 | 12/1977 | Bodor et al. | 424/266 |
| 4,202,323 | 5/1980 | Zweig et al. | 424/1 |
| 4,206,220 | 6/1980 | Sloan | 424/274 |
| 4,242,330 | 12/1980 | Hussain et al. | 424/235 |

OTHER PUBLICATIONS

The Friday Evening Post, Aug. 14, 1981, Health Center Communications, Univ. of Fla., Gainesville, Fla.
Chemical and Engineering News, Dec. 21, 1981, pp. 24-25.
Science News, Jan. 2, 1982, vol. 121, #1, p. 7.
Brewster III, Dis. Abst. Int. B, vol. 43, #9, p. 2910B.
Bodor et al., Science, vol. 190, (1975), pp. 155-156.
Bodor et al., Science, vol. 214, (1981), pp. 1370-1371.
Bodor et al., J. Pharm. Sci., vol. 67, (1978), pp. 685-687.
Shek et al., J. Med. Chem., vol. 19, (1976), pp. 113-117.

Primary Examiner—Christine M. Nucker
Attorney, Agent, or Firm—Dennis P. Clarke

[57] ABSTRACT

Centrally acting drug species are site-specifically/sustainedly delivered to the brain by administering to a patient in need of such treatment a therapeutically effective amount of the target drug species [D] tethered to a reduced, blood-brain barrier penetrating lipoidal form [D-DHC] of a dihydropyridine⇌pyridinium salt type redox carrier. Oxidation of the dihydropyridine carrier moiety in vivo to the ionic pyridinium salt type drug/carrier entity [D-QC]+ prevents elimination thereof from the brain, while elimination from the general circulation is accelerated, and subsequent cleavage of the quaternary carrier/drug species results in sustained delivery of the drug [D] in the brain and facile elimination of the carrier moiety [QC]+.

25 Claims, 6 Drawing Figures

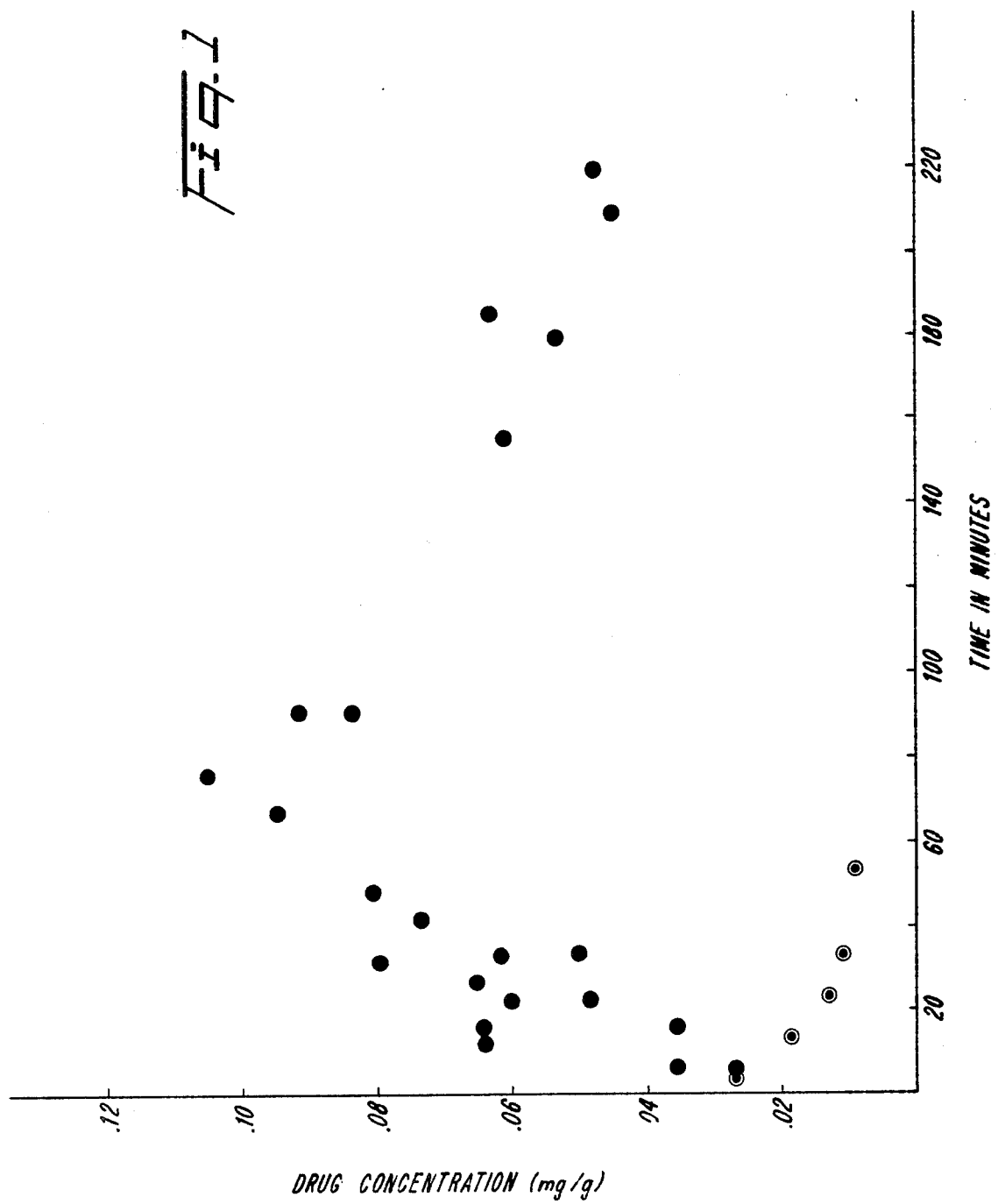

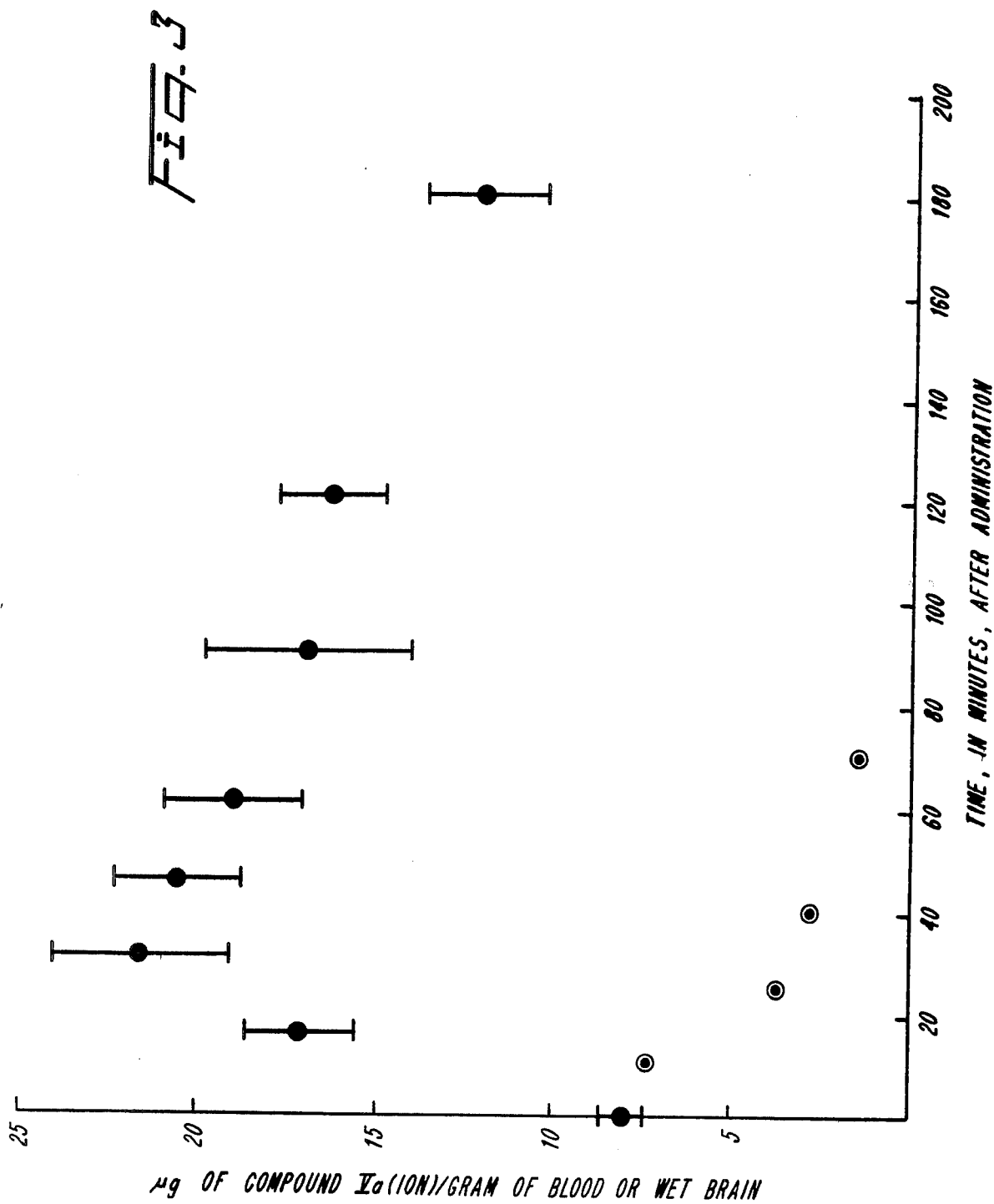

BRAIN-SPECIFIC DRUG DELIVERY

BACKGROUND OF THE INVENTION

1. Historical

The invention(s) described herein was/were made in the course of, or under, a grant from the National Institutes of Health.

2. Field of the Invention

The present invention relates to a dihydropyridine/-pyridinium salt type of redox system for the site-specific or sustained delivery (or both) of a wide variety of drug species to the brain. More especially, this invention relates to the discovery that a biologically active compound coupled to a lipoidal carrier moiety comprising a dihydropyridine nucleus readily and easily penetrates the blood-brain barrier ("BBB") and attains increased levels of concentration in the brain; oxidation of the dihydropyridine carrier moiety in vivo to the ionic pyridinium salts prevents its elimination from the brain, while elimination from the general circulation is accelerated, and subsequent cleavage of the quaternary carrier/drug species results in sustained delivery of the drug in the brain and facile elimination of the carrier moiety.

3. Description of the Prior Art:

The delivery of drug species to the brain is ofttimes seriously limited by transport and metabolism factors and, more specifically, by the functional barrier of the endothelial brain capillary wall deemed the blood-brain barrier, BBB. Site-specific delivery and sustained delivery of drugs to the brain are even more difficult, and to date no useful simple or generic techniques to achieve such phenomena are known to the art.

Indeed, the barriers separating plasma from the brain and cerebrospinal fluid (CSF) are complex systems involving passive and active transport and subserve a number of important functions. The boundary between plasma and the central nervous system (CNS) is much less permeable than that between plasma and other tissue cells to a variety of water soluble substances, such as organic electrolytes, organic acids and bases, as well as to large molecules such as proteins. Such a barrier also provides a path for clearance from the brain of the breakdown products of cellular metabolism. The CNS and its fluids can be considered basically a three-compartment system: the blood or the plasma, CSF and brain tissue. There is a diffusion-controlled exchange between CSF and the extracellular fluid (CF) of the brain. It has also been suggested that the permeabilities of blood-CSF and blood-brain barriers are practically identical with respect to drugs and other foreign substances. Mayer et al, *J. Pharmacol. and Exp. Therap.*, 125, 185 (1959).

The BBB is, moreover, basically the result of the fact that the endothelial cells in the brain capillaries are joined by continuous, tight intercellular junctions, such that material has to pass through the cells rather than between them in order to move from blood to brain. It is interesting that there are areas within the brain, such as the subfornical body and the postremia in which the capillary cells are not closely linked so that they lack the characteristics of the BBB. They provide for the entry of small amounts of compounds which would not ordinarily enter the barriers. Hoffmann and Olszewzki, *Neurology (Minneap.)*, 11, 1081 (1961).

Foreign compounds which enter organs other than the central nervous system with ease, may penetrate the CNS slowly or hardly at all. A number of theories concerning the nature of the barrier have been proposed. The widely accepted concept describes the boundary as a fat-like layer interspersed with small pores, although the BBB is not a simple, anatomically well-defined unitary physical entity. Shuttleworth, *Prog. Exp. Tumor Res.*, 17, 279 (1972). Penetration of such a barrier may occur by several processes: lipid soluble substances may passively penetrate into the cells, while small molecules such as water and urea may pass through the pores. In addition to these simple physical processes, carrier-mediated and active transport processes govern the movement of many molecules through the BBB. Thus, it is generally accepted that lipid solubility, degree of ionic dissociation or protonation and the ability of temporary combination with membrane constituents affect delivery through the BBB. It has been shown, for example, that in the class of barbiturates, a quantitative correlation could be established between their ease to pass into the brain (as reflected by the different times of onset of anesthetic action) and their lipid/water partition coefficient. Mark et al, *J. Pharmacol. and Exp. Therap.*, 123, 79 (1957). The role of lipid solubility in drug penetration through the BBB is also exemplified by the better absorption of the sparingly water-soluble thiamine propyl disulfide (TPD) as compared to the water-soluble thiamine hydrochloride (THCl). Thomson et al, *Ann. Int. Med.*, 74, 529 (1971). Some materials such as glucose and amino acids are transported by active mechanism, characterized by saturation, bidirectional molecular specificity, bidirectional competitive inhibition and bidirectional countertransport. Fishman, *Am. J. Physiol.*, 206, 836 (1964).

Changes in permeability of the BBB can be caused by several pathological and toxicological processes. Pardridge, Connor and Crawford, *CRC Crit. Rev. Toxicol.*, 179 (1975). A general increase in the barrier permeability, such as a nonspecific breakdown of the barrier has, however, severe consequences, including cerebral edema.

It too is well documented that the BBB is relatively impermeable to the ionized forms of drugs and other molecules. Drugs which are weak organic electrolytes appear to pass from blood to CSF to reach a steady state ratio characteristic of each molecule according to its $pK_a$ and the existence of a normal pH gradient between blood and CSF. It is clear that it is the most difficult for quaternary pyridinium or ammonium salts to penetrate the BBB.

And removal of substances from the brain and CSF is obviously a significant factor in regulating drug concentrations in the CNS. There are several efflux processes: bulk flow via the arachnoid villi, diffusion of lipid soluble substances into brain and blood, active transport and metabolism by adjacent meninges. Once a drug or metabolite enters the CSF from blood or brain by simple diffusion, it may rapidly be removed, either by nonselective bulk flow or by active transport mechanism associated with the choroid plexus or other nondefined structures in the CSF compartment. It is generally accepted that highly lipid-soluble drugs leave the CSF more rapidly than poorly lipid-soluble ones, but the barrier to passage of compounds from CSF has only superficial similarity to the blood-CSF barrier.

Drug elimination processes from the brain are significantly directly related to drug accumulation in the brain. It is generally assumed that efflux in the opposite direction involves almost the same processes as for entry, except that the role of the bulk flow and the metabolic processes in the brain are not to be overlooked.

The two elimination processes studied in the earlier literature and which can be said to have a certain bearing on the present invention involve elimination from the brain of ionic species. Thus, it is found that non-metabolized ionic species, such as the acetate ion, have a three times slower elimination rate from the CSF than from the blood. Freundt, *Arz. Forsch.*, 23, 949 (1973). An even more dramatic change in the elimination rate was found in the case of a quaternary piperidinium salt. The quaternary salt, formed in situ after delivery of a haloalkylamine, which undergoes cyclization to the quaternary salt, in the brain, as well, was found to have an at least ten times slower elimination rate from the brain than from the rest of the body. It was concluded by the authors (Ross and Froden, *Eur. J. Pharmacol.*, 13, 46 [1970]) that the outflow rate of the quaternary salt corresponded to the inflow rate. Similar results were obtained for the erythrocytes: the efflux of the quaternary salt was very slow. Ross, *J. Pharm. Pharmacol.*, 27, 322 (1975).

And while it too has been suggested to deliver a drug species, specifically N-methylpyridinium-2-carbaldoxime chloride (2-PAM), into the brain, the active nucleus of which in and of itself constituting a quaternary pyridinium salt, by way of the dihydropyridine latentiated prodrug form thereof, such approach is conspicuously delimited to relatively small molecule quaternary pyridinium ring-containing drug species and does not provide the overall ideal result of brain-specific, sustained release of the desired drug, with concomitant rapid elimination from the general circulation, enhanced drug efficacy and decreased toxicity. Hence, no "trapping" in the brain of the 2-PAM formed in situ results, and obviously no brain-specific, substained delivery occurs as any consequence thereof: the 2-PAM is eliminated as fast from the brain as it is from the general circulation and other organs. Compare my U.S. Pat. Nos. 3,929,813 and 3,962,447; Bodor et al, *J. Pharm. Sci.*, 67, No. 5, 685 (1978). It has also been speculated to deliver, e.g., an antitumor agent into the brain by utilizing a dihydropyridine/pyridinium redox carrier moiety therefor, but this particular hypothesis necessarily entails derivatizing the dihydropyridine/pyridinium carrier with a substituent $R_1$ itself critically designed to control the release rate of the active drug species from the quaternary derivative thereof, as well as being critically functionally coordinated with the particular chemical and therapeutic activity/nature of the antitumor drug species itself; Bodor et al, *J. Pharm. Sci.*, supra.

Accordingly, acutely serious need exists in this art for a truly effective generic but nonetheless flexible method for the site-specific, or sustained delivery, or both, of drug species to the brain, while at the same time avoiding the aforesaid noted and notable disadvantages and drawbacks associated with penetration of the blood-brain barrier, with dihydropyridine latentiated prodrug forms of drug species themselves comprising a pyridinium salt active nucleus, and with the necessity for introducing critically coordinated and designed, release rate-controlling substituents onto any particular drug carrier moiety.

SUMMARY OF THE INVENTION

Accordingly, a major object of the present invention is the provision of a generic method for the specific and/or target enhanced delivery to the brain of a wide variety of drug species and to achieve brain-specific drug delivery by effecting the bidirectional transport of the drug species into and out of the brain employing dihydropyridine⇌pyridinium salt carrier type redox systems.

Another object of the invention is to provide for brain-specific drug delivery utilizing a dihydropyridine⇌pyridinium salt carrier type redox system, which drug/carrier system is characterized by enchanced drug efficacy and decreased toxicity. Indeed, consistent herewith systemic toxicity is significantly reduced by accelerating the elimination of the drug/quaternary carrier system, and even central toxicity is reduced by providing a low level, sustained release of the active drug species in the brain.

Yet another object of this invention is the provision of a chemical delivery system for the site-specific and sustained release of drug species to the brain, and one in which a special pro-prodrug reduced form of an active drug species is actually delivered to the body of a patient, not a prodrug as such and not a drug/carrier entity necessarily comprised of critically tailored release rate-controlling substituent(s).

Briefly, the present invention features a dihydropyridine⇌pyridinium salt carrier redox system for the specific and sustained delivery of drug species to the brain according to the following Scheme 1:

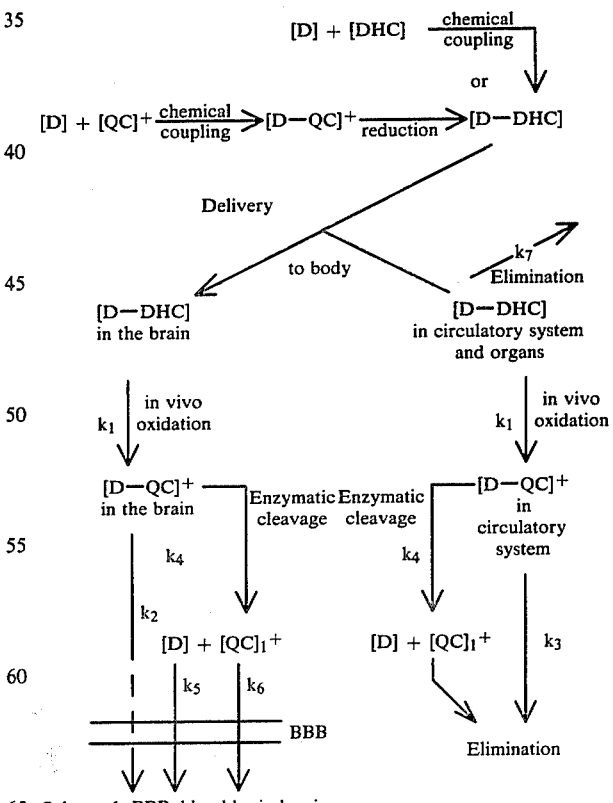

Scheme 1: BBB, blood-brain barrier.

Consistent with the foregoing Scheme 1, any drug species [D] is coupled to a quaternary pyridinium salt carrier [QC]+ and the prodrug [D-QC]+ which results is then reduced chemically to the lipoidal dihydro pro-prodrug from [D-DHC]. Alternatively, the drug species [D] can be directly coupled to the dihydro carrier [DHC] in certain instances to yield said pro-prodrug form [D-DHC]. After administration of the [D-DHC] in vivo, it is rapidly distributed throughout the body, including the brain. The dihydro form [D-DHC] is then in situ oxidized (rate constant, $k_1$) (by the NAD$\rightleftharpoons$NADH system) to the ideally inactive original [D-QC]+ quaternary salt prodrug, which, because of its ionic, hydrophilic character, is rapidly eliminated from the general circulation of the body, while the blood-brain barrier prevents its elimination from the brain ($k_3>>k_2$; $k_3>>k_7$). Enzymatic cleavage of the [D-QC]+ that is "locked" in the brain effects a sustained delivery of the drug species [D], followed by its normal elimination ($k_5$), metabolism. A properly selected carrier [QC]+ will also be rapidly eliminated from the brain ($k_6>>k_2$). Because of the facile elimination of [D-QC]+ from the general circulation, only minor amounts of drug are released in the body ($k_3>>k_4$); [D] is released primarily in the brain ($k_4>k_2$). The overall result is a brain-specific, sustained release of the target drug species. Cf. Bodor et al, *Science,* 214, 1370 (1981); *C&EN,* 24 (Dec. 21, 1981).

DETAILED DESCRIPTION OF THE INVENTION

Figure 2A:
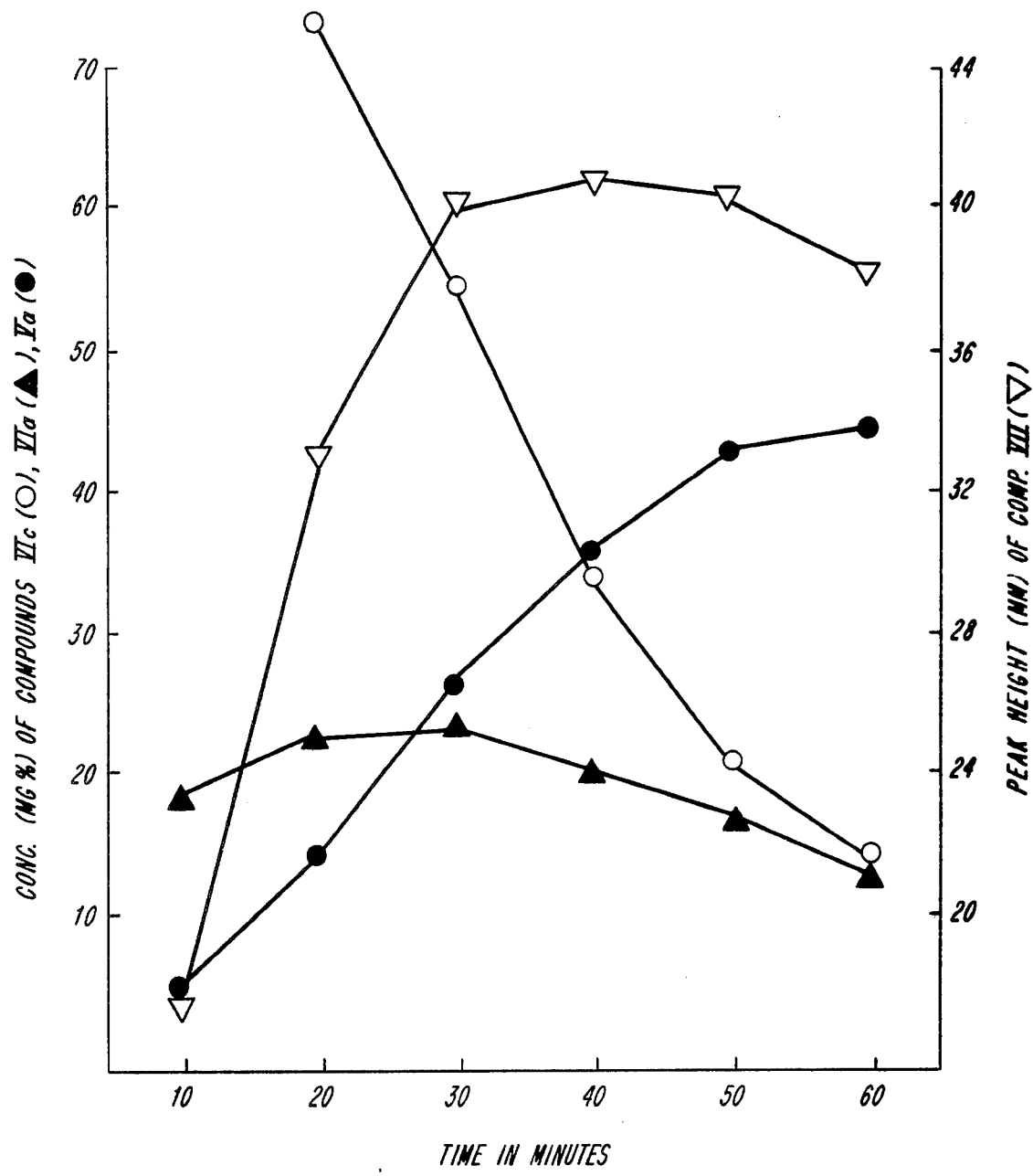

More particularly according to this invention, there is hereby provided a generic method for specific and/or target enhanced delivery to the brain of a wide variety of centrally acting drug species, such brain-specific drug delivery being effected via the bidirectional transport of the drug species into and out of the brain by means of dihydropyridine$\rightleftharpoons$pyridinium salt carrier type redox systems.

Exemplary such centrally acting drug species are the CNS-amines and other nervous system agents, whether sympathetic or parasympathetic, e.g., phenylethylamine, dopamine, tyramine, L-DOPA, muscle relaxants, tranquilizers and antidepressants, e.g., benzodiazepine tranquilizers such as diazepam and oxazepam, mild and strong analgesics and narcotics, sedatives and hypnotics, narcotic antagonists, vascular agents, stimulants, anesthetics, small peptides, such as the di-, tri, tetra- and pentapeptides, and other small 6–20 aminoacid unit containing peptides, e.g., the enkephalins (for example, Tyr-Gly-Gly-Phe-Leu), which, besides being analgesics, initiate epileptic activity in the brain at doses that are about tenfold lower than for effecting analgesic activity, larger peptides, such as pituitary hormones and related agents, antiepileptic and anticonvulsant drugs generally, hormones, such as the steroid hormones, e.g., estradiol, testosterone, 17 α-ethynyl testosterone, etc. (recent studies on histological mapping of hormone-sensitive and specific steroid binding cells in the brain have underscored the importance of the steroid action in the brain on sexual behavior), amphetamine-like drugs, anticancer and anti-Parkinsonism agents, anti-hypertensives, agents to enchance learning capacity and the memory processes, including treatment of dementias, such as Alzheimer's disease, antibacterials, centrally active hypotensive agents, diagnostic agents, such as radiopharmaceuticals, monoamine oxidase (MAO) inhibitor drugs, phenothiazines, CNS or brain important/essential amino acids, such as tryptophane, and any like centrally acting compounds.

By "centrally acting" drug species, active agent or compound as utilized herein, there is of course intended any drug species or the like, the principal pharmacological activity of which is CNS and a result of direct action in the brain.

Other illustrative ultimate species of drug entities falling within the immediately above drug families are amphetamine, dextroamphetamine, levamphetamine, methamphetamine, phenmetrazine, phentermine, acetaminophen, aspirin, codeine, oxycodone, pentazocine, anilerdine, hydromorphone, morphine, oxymorphone, desipramine, nortriptyline, opipramol, protriptyline, clonidine, methyldopa, biperiden, cycrimine, procyclidine, tranylcypromine, acetophenazine, carphenazine, fluphenazine, perphenazine, piperacetazine, chlordiazepoxide, clorazepate, nitrazepam, temazepam, haloperidol, clopenthixol, norepinephrine, nalorphine, naloxone, hydralazine, ethoton, phenobarbital, aminoglutethimide, ethamiran, bemegride, amiphenazole, iopydol, iodopyracet, iodouppurate, iodamide, iopanic acid, ephedrine, pseudoephedrine, oxymetazoline, phenylephrine, estrogen, amoxicillin, ampicillin, amobarbital, trihexyphenidyl, reserpine, hydroxyzine, chlortetracycline, oxacillin, clindamycin, flurazepam, phenytoin, meperidine, propoxyphene, glutethimide, triamterene, bethanidine, guanethidine, imipramine, propranolol, lincomycin, nalidixic acid, methylprylon, dicloxacillin, butalbital, and the like.

It too will be appreciated that by "dihydropyridine carrier" or "[DHC$\rightleftharpoons$, there is intended any nontoxic carrier moiety comprising, containing or including the dihydropyridine nucleus, whether or not a part of any larger basic nucleus, and whether substituted or unsubstituted, the only criterion therefor being capacity for both BBB-penetration and in vivo oxidation thereof to the corresponding quaternary pyridinium salt carrier [QC]+. As aforesaid, the ionic pyridinium salt drug/carrier prodrug entity [D-QC]+ which results from such in vivo oxidation is prevented from efflux from the brain, while elimination from the general circulation is accelerated. Subsequently, the covalent or equivalent bond coupling the drug species [D] to the quaternary carrier [QC]+ is metabolically cleaved which results in sustained delivery of the drug [D] in the brain and facile elimination of the carrier moiety [QC]+. Such "covalent or equivalent bond" between the drug and the quaternary carrier can be a simple direct chemical bond, e.g., an amide, an ester, or any other like bond, or same can even be comprised of a linking group or function, e.g., a thiazolidine bridge or a peptide linkage, typically necessitated when the drug species is not susceptible to direct chemical coupling to either the dihydropyridine carrier or the quaternary carrier. Nonetheless, the bond in the formulae [D-QC]+ and [D-DHC] is intended to be, as is hereby defined as inclusive of all such alternatives. And the cleavage of the [D-QC]+ prodrug to sustainedly deliver the drug species [D] in the brain with concomitant facile elimination of the carrier moiety [QC]+ is characteristically enzymatic cleavage, e.g., by esterase, amidase, cholinesterase, hydrolytic enzyme, or peptidase, albeit any type of in brain cleavage which might result, whether enzymatic, metabolic or otherwise, of course remains within the ambit of this invention. Thus, the drug release late controlling parameter of the subject pro-prodrugs is imparted simply via the cleavable bonding between drug and carrier, and not by any release rate controlling substituent(s).

In one embodiment according to this invention, simple nontoxic carrier systems [D-QC]+⇌[D-DHC] are envisaged, utilizing a wide variety of models of D, such as those above outlined. Representative such carrier systems and models are:

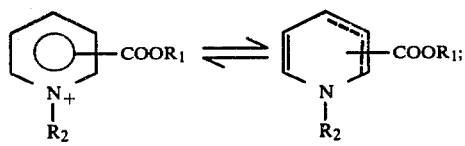

$R_1O-$ or $R_1NH- = D$

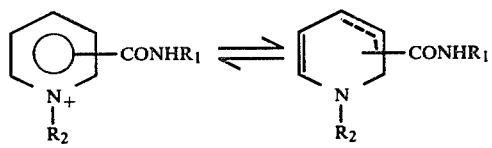

wherein $R_2$ is simply alkyl or benzyl, albeit virtually any other effective substituent is intended, and $R_1$ can be, for example, a $C_1-C_{12}$ alkyl or aralkyl moiety to comprise a drug species such as dopamine, other CNS-amines, or indeed any of the brain-acting active agents.

Exemplary of such simple carrier systems are N-alkyl nicotinamide and nicotinate ester derivatives, tethered to such drug species as phenylethylamine, decyl and dodecylamine, and long chain alcohols such as dodecanol. Thus, the corresponding quaternary pyridinium salts (general formula I) were synthesized from nicotinic acid and the model compounds followed by quaternization (Table I):

TABLE I

Synthesized Simple Carrier Type Quaternary Pyridinium Derivatives (I) and the Corresponding Dihydropyridines (II)

| Compound | $R_1$ | $R_2$ | X |
|---|---|---|---|
| I and II a | —$CH_3$ | —NHCH$_2$CH$_2$—⌬ | I(CH$_3$SO$_3^-$) |
| b | —$CH_3$ | —NH(CH$_2$)$_9$CH$_3$ | I |
| c | —$CH_3$ | —NH(CH$_2$)$_{11}$CH$_3$ | I |
| d | —CH$_2$C$_6$H$_5$ | —NHCH$_2$CH$_2$—⌬ | Br |
| e | —CH$_2$C$_6$H$_5$ | —NH(CH$_2$)$_9$CH$_3$ | Br |
| f | —CH$_2$C$_6$H$_5$ | —NH—(CH$_2$)$_{11}$CH$_3$ | Br |
| g | —CH$_3$ | —O(CH$_2$)$_{11}$CH$_3$ | I(CH$_3$SO$_3^-$) |
| h | —CH$_2$C$_6$H$_5$ | —O(CH$_2$)$_{11}$CH$_3$ | Br |

Compounds I a-h were characterized by elementary analysis, ir, UV and NMR spectra.

The corresponding dihydropyridine derivatives (II a-h) were synthesized employing the dithionite reduction method. The 1,4-dihydropyridine structure was established based on spectral (UV and NMR) and chemical properties. The dihydro derivatives, II a-h were determined to be relatively stable and were quantitatively oxidized back to the quaternary derivatives I by $H_2O_2$ or $AgNO_3$ (based on spectral data and characterization of the isolated products). Oxidation of compounds II takes place in biological fluids, as well. Thus, incubation at 37° C. in fresh human blood for 15 minutes resulted in quantitative conversion of IIa to Ia, evidencing the effectiveness of the redox system in the subject specific brain delivery of drugs. Most of the obtained dihydro derivatives II were oily compounds, simple β-protonated enamine salt formation was unsuccessful in certain instances, as some nucleophilic addition and dimerization reactions occur.

Further studies were conducted upon the aforesaid compounds wherein $R_2$ was phenylethylamine, and $R_1$ was either methyl or benzyl, namely:

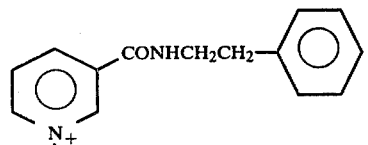

Ia R = CH$_3$; Id R = CH$_2$—C$_6$H$_5$

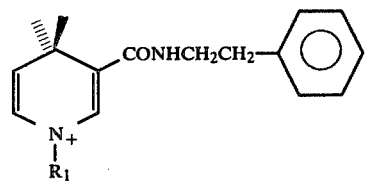

IIa R = CH$_3$; IId R = CH$_2$C$_6$H$_5$

In vitro studies in biological fluids indicated facile oxidative conversion of the dihydro forms to the quaternary derivatives as hereinafter set forth in Table II.

The N-methyl derivatives IIa⇌Ia were selected for in vivo studies due to the relative ease of interconversion. Thus, the dihydro derivative IIa was administered i.v. to rats. The animals were sacrificed at various time intervals following administration and the brain and blood were analyzed for the quaternary compound Ia using an HPLC method. The results summarized in FIG. 1 confirm the mechanism shown in Scheme 1. Thus, the quaternary salt Ia disappeared quickly from the blood. On the contrary, the concentration of Ia increased in the brain steadily, reaching a maximum at about 80 minutes following administration. The next descending portion indicates a half-life for disappearance of Ia of $t_{\frac{1}{2}}=2.15$ hr. In a separate experiment using a homogenate of freshly perfused rat brain, a half-life of 3 hr was found for the cleavage of Ia→C$_6$H$_5$—CH$_2$CH$_2$NH$_2$+trigonelline. Thus, the descending portion corresponds mainly to the sustained delivery of phenethylamine in the brain. Hence, all criteria set forth in Scheme 1 were confirmed: one simple i.v. injection of a drug coupled to a dihydropyridine carrier system resulted in accumulation of the corresponding drug-quaternary carrier species in the brain, followed by a sustained release of the drug in the brain, while the drug-quaternary carrier system was rapidly eliminated from the blood. When the quaternary derivative Ia was administered at equivalent dose levels, no amount could be detected in the brain of rats.

In said FIG. 1 is plotted the concentration of 1-methyl-3-(N-β-phenethyl)-carbamoyl-pyridinium salt in the brain (●) and the blood (◉) of rats following administration of the 1-methyl-3-(N-β-phenethyl)-carbamoyl-1,4-dihydropyridine (IIa).

In another embodiment of the invention, quaternary model compounds of the type III were also synthesized and the rates of oxidation of the corresponding dihydro-derivative IV to III were also studied.

Two representative compounds were selected for in vitro conversion studies in brain homogenate and in blood. One, IVa, was a symmetrical bisamide, while IVb was a mixed, half-ester, half-amide. The rates of interconversion set forth in the Table II which follows indicate that, as expected, compounds of type IV are much more stable than the monosubstituted congeners, although substitution in other positions and/or with less electron withdrawing groups could alter the stability. Nevertheless, based on these results, the original trigonelline type system was used to confirm the brain delivery of other biological amines, such as dopamine and tyramine.

In yet another embodiment of the invention, the Scheme 1 mechanism was confirmed utilizing dopamine as the target drug species and a trigonelline type carrier system, with the catechol moiety thereof in certain instances being acylated, e.g., acetylated or pivalylated. In vitro and in vivo determinations were carried out on the corresponding V⇌VI conversion:

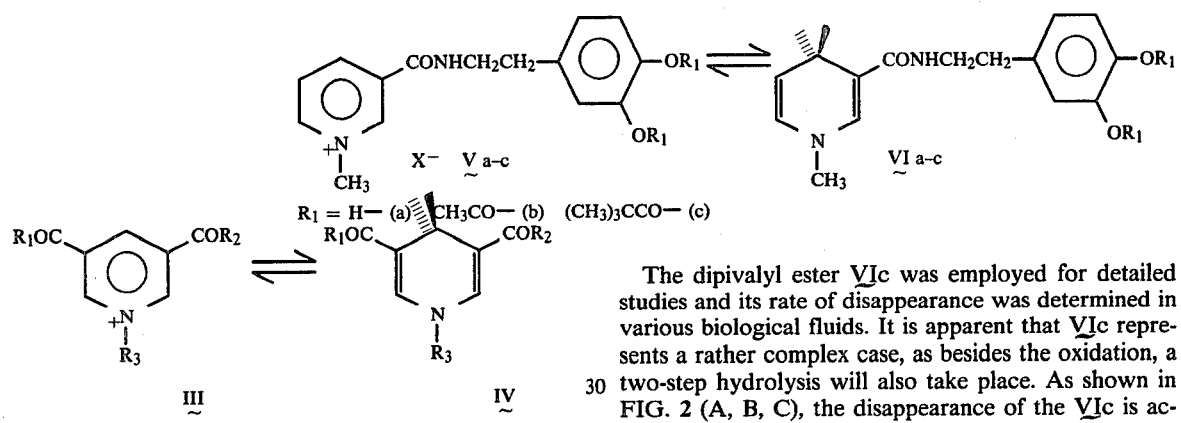

Figure 2B:
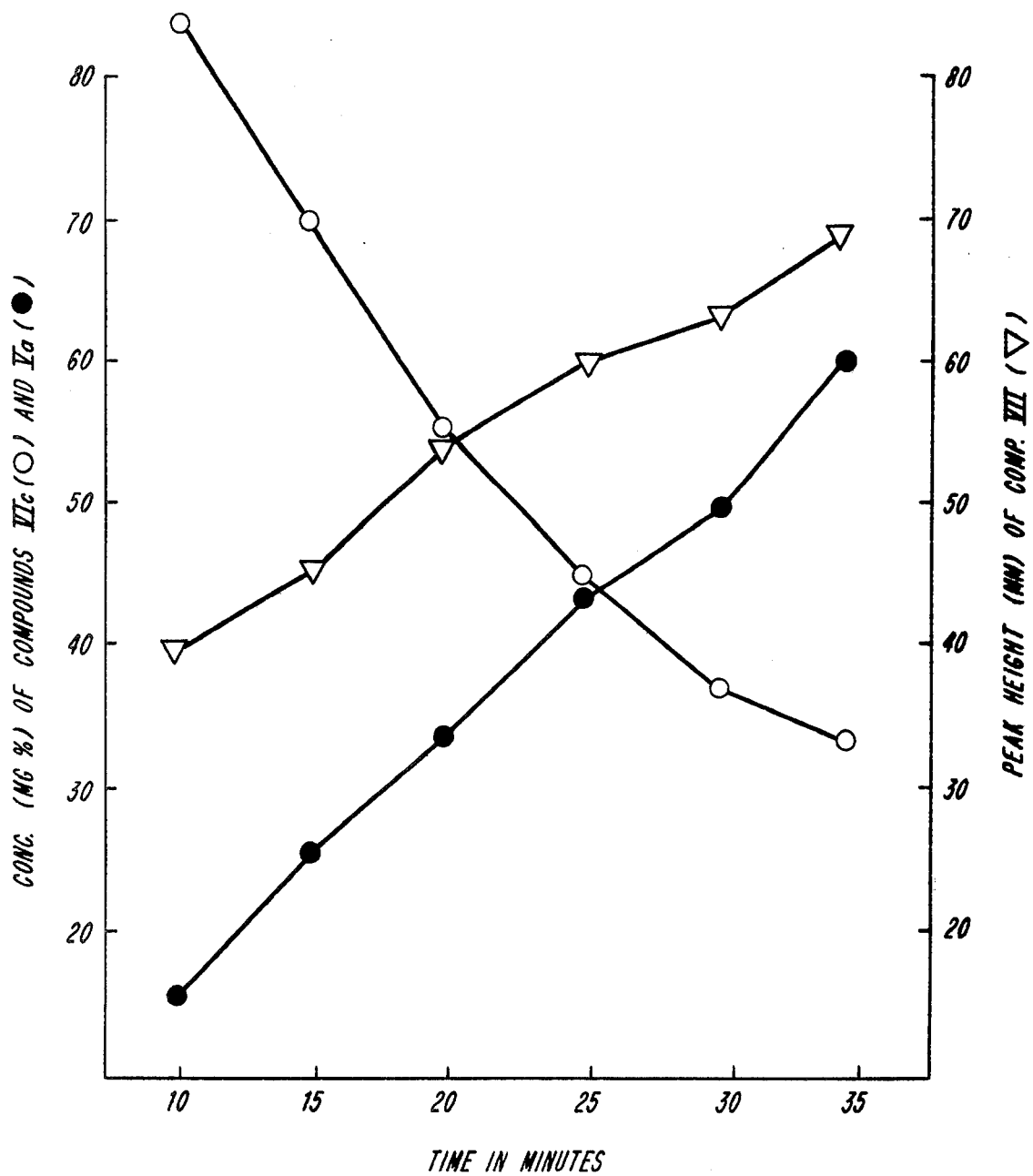
Figure 2C:
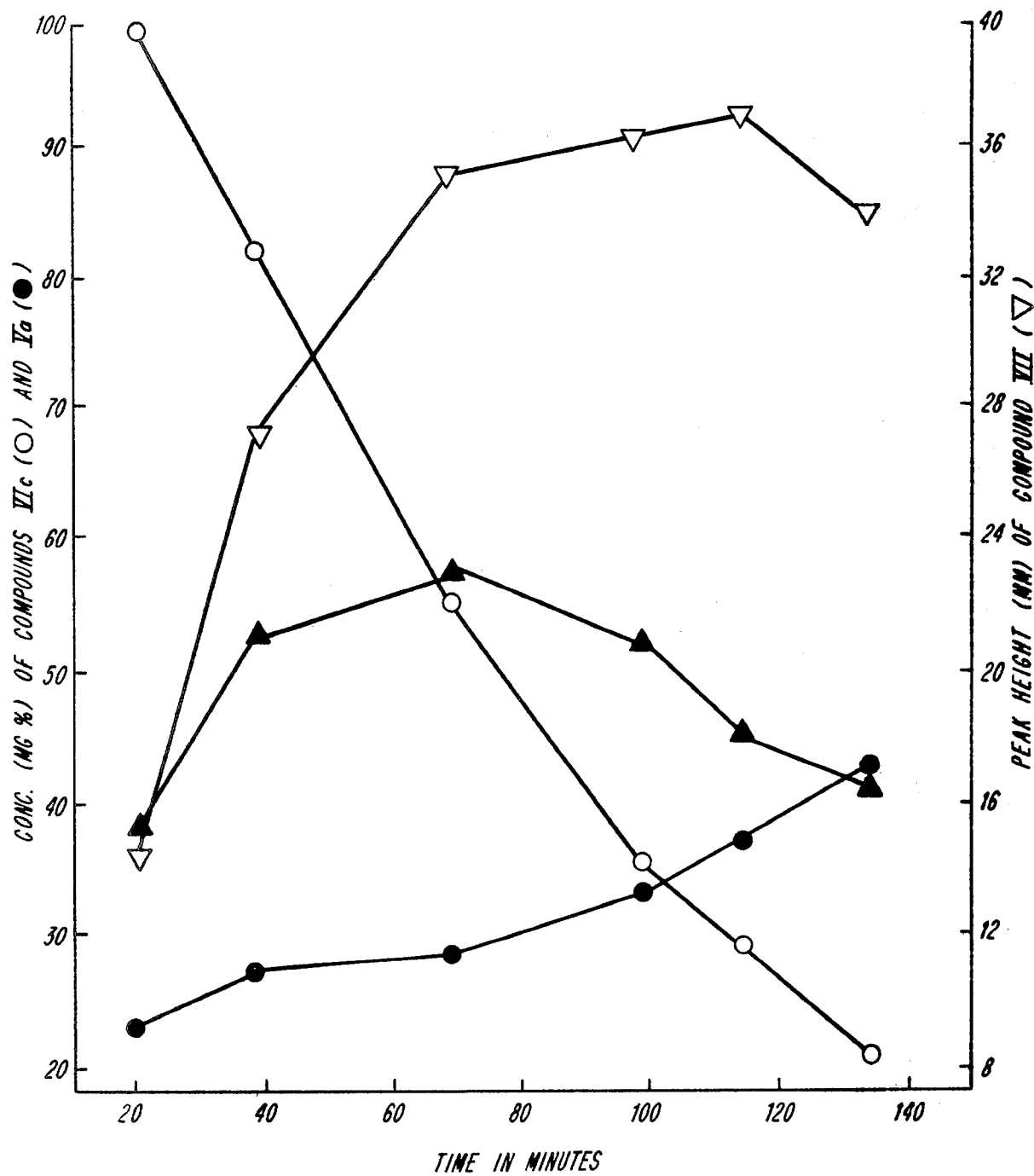

The dipivalyl ester VIc was employed for detailed studies and its rate of disappearance was determined in various biological fluids. It is apparent that VIc represents a rather complex case, as besides the oxidation, a two-step hydrolysis will also take place. As shown in FIG. 2 (A, B, C), the disappearance of the VIc is accompanied by formation of some monoester VII and the dihydroxy dihydro form VIa, but a steady increase in the concentration of the dopamine-precursor Va was observed in all cases. Scheme 2 reflects the interconversion of the possible components. The dipivalyl quaternary VIII could not be detected in the reaction mixtures. Compounds Va and c and VIa and c were prepared and identified in the mixture. The half-ester VII was tentatively identified based upon its behavior.

Scheme 2

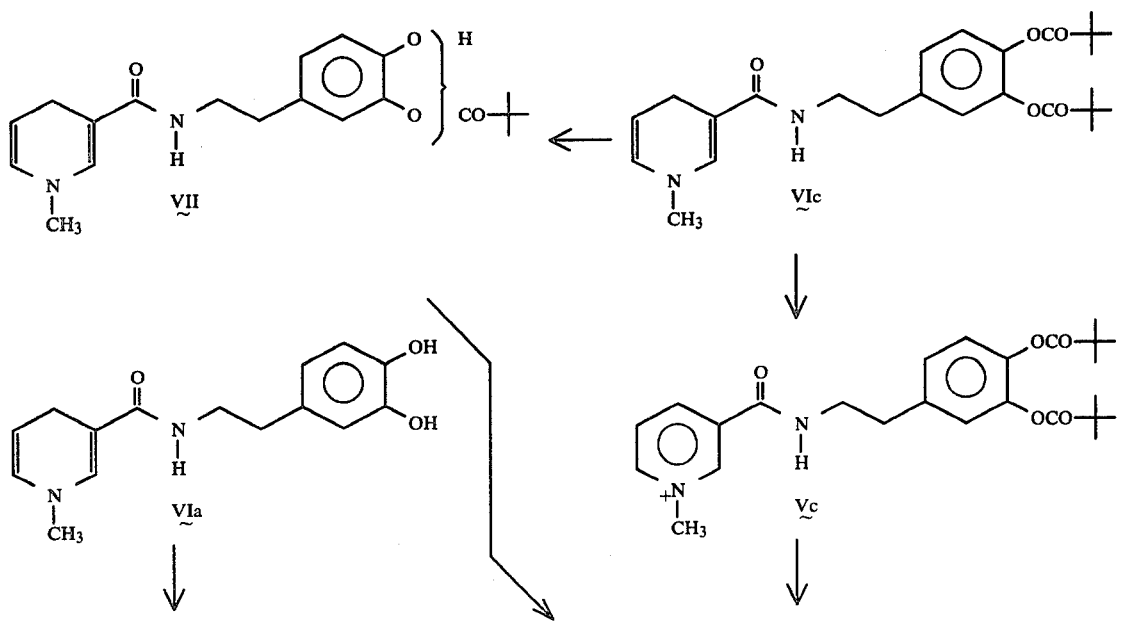

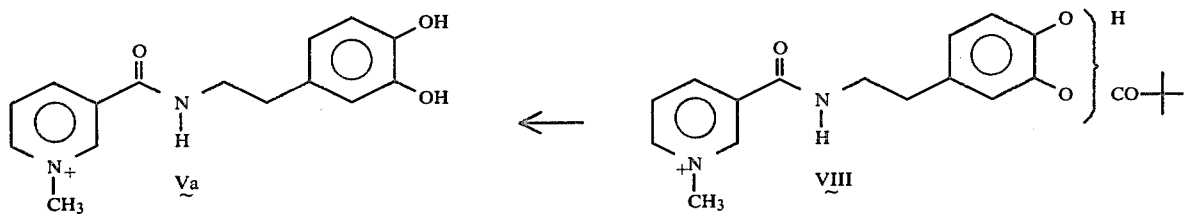

In said FIG. 2, plotted are the time course of 1-methyl-3-{N-[β-(3,4-dipivalyloxyphenyl)-ethyl}carbamoyl-1,4-dihydropyridine (VIc, ○) in brain homogenate (A), whole blood (B) and plasma (C) at 37° C. The products are the monopivalyl-dihydro derivative VII (∇), the dihydro-dopamine derivative VIa (▮) and the quaternary dopamine precursor Va (●).

The apparent half-lives for the disappearance of VIc were calculated (although the process does not truly follow first order kinetics, the data very closely fit a pseudo-first order process). The obtained values (organs): 51 min (plasma), 17 min (brain homogenate), 18 min (whole blood) and 6 min (liver homogenate) are comparable to the corresponding values obtained for the phenylethyl-derivative IIa. The in vitro determinations confirmed whether the dopamine derivative Va was forming as the main product of the various possible interconversion routes. Based on the results, in vivo studies using rats were performed, following the appearance and disappearance of Va in blood and brain. FIG. 3 summarizes these results. Similarly to the case of phenethylamine, following administration of VIc the dopamine derivative Va attains high concentrations in the brain, having maximum at about 30 min, followed by slow decrease in concentration, while the quaternary derivative Va disappears rapidly from the blood.

In said FIG. 3 are plotted time dependent concentration of 1-methyl-3-{N-[β-(3,4-dihydroxyphenyl)]}carbamoyl pyridinium salt (Va) in the brain (●) and blood (⊙) of rats following administration of 1-methyl-3-{N-[β-(3,4-dipivalyloxyphenyl)ethyl]}-carbamoyl-1,4-dihydropyridine (VIc). Dose of VIc: 50 mg/kg (equivalent to 31 mg/kg of Va).

In yet another embodiment of the invention, like synthesis of the analogous tyramine system was carried out, and the corresponding determinations made. Such tyramine system is represented as follows:

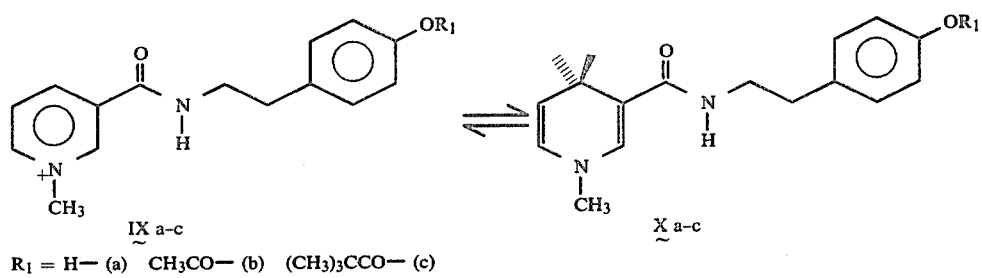

$R_1 =$ H— (a)  $CH_3CO$— (b)  $(CH_3)_3CCO$— (c)

Similarly, syntheses and like determinations as regards the redox carrier linked enkephalins were carried out. First synthesized was the known leucine enkephalin XI. The quaternary pyridinium analog XII, the corresponding O-benzyl ether XIII and the amide XIV were next synthesized.

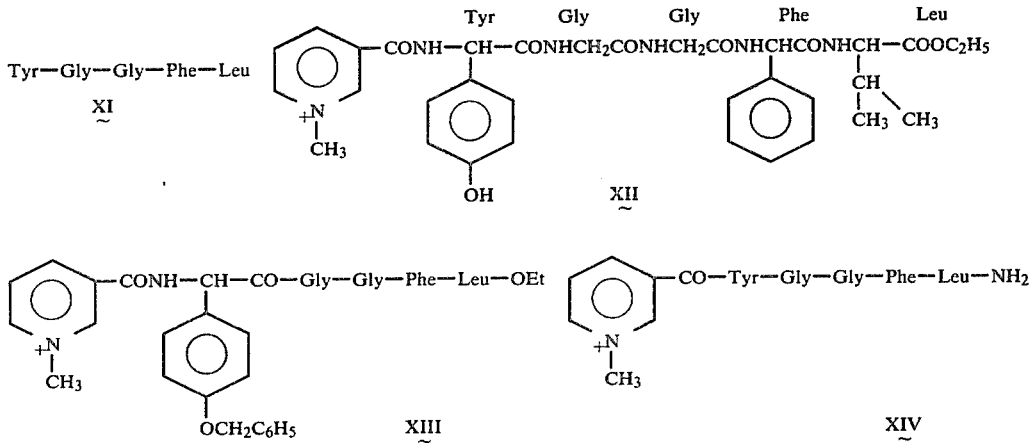

The O-benzyl pentapeptide ethyl ester derivative of XI was synthesized sequentially and then coupled with nicotinic acid, followed by methylation. Alternate methods involved introduction of carrier at earlier stage in the synthesis. The reduction of XII and XIII resulted in a mixture of products due to the base sensitivity of the ester. Likewise prepared were the corresponding leucinol trigonelline ester X̲V̲ and its dihydro derivatives X̲V̲I̲.

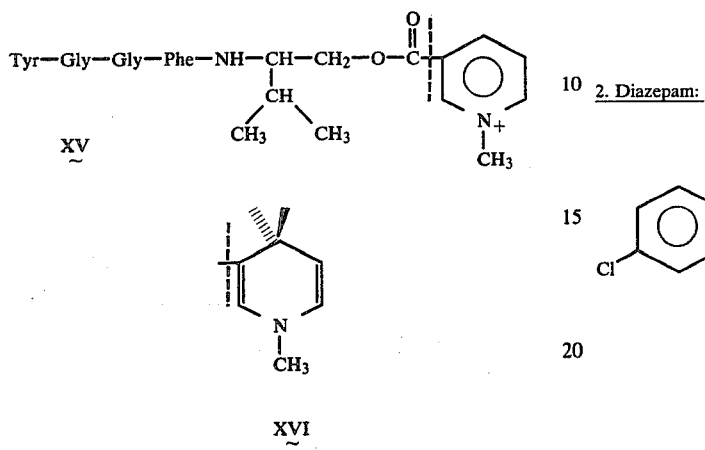

Thus, the site-specific brain delivery of the enkephalins for the treatment of epilepsy was established consistent with the Scheme 1, as was their analgesic activity.

Too, the brain-delivery of the steroids was established, in particular the trigonelline ester of testosterone, and corresponding dihydro form thereof, as well as the following prodrugs and their counterpart pro-prodrugs:

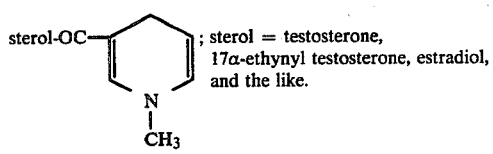

; sterol = testosterone, 17α-ethynyl testosterone, estradiol, and the like.

Similarly as regards the benzodiazepine tranquilizers, e.g.:

1. Oxazepam:

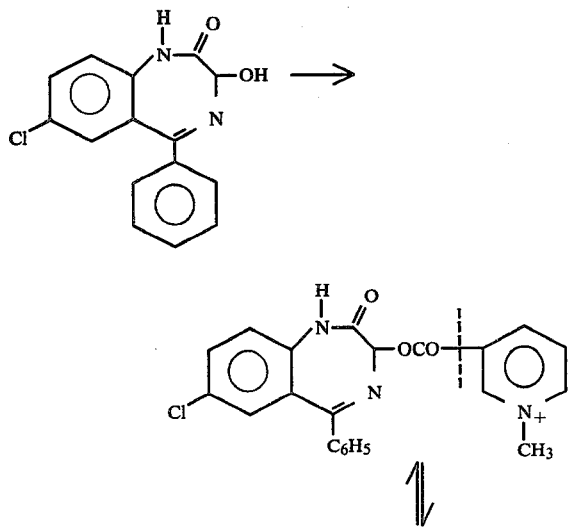

2. Diazepam:

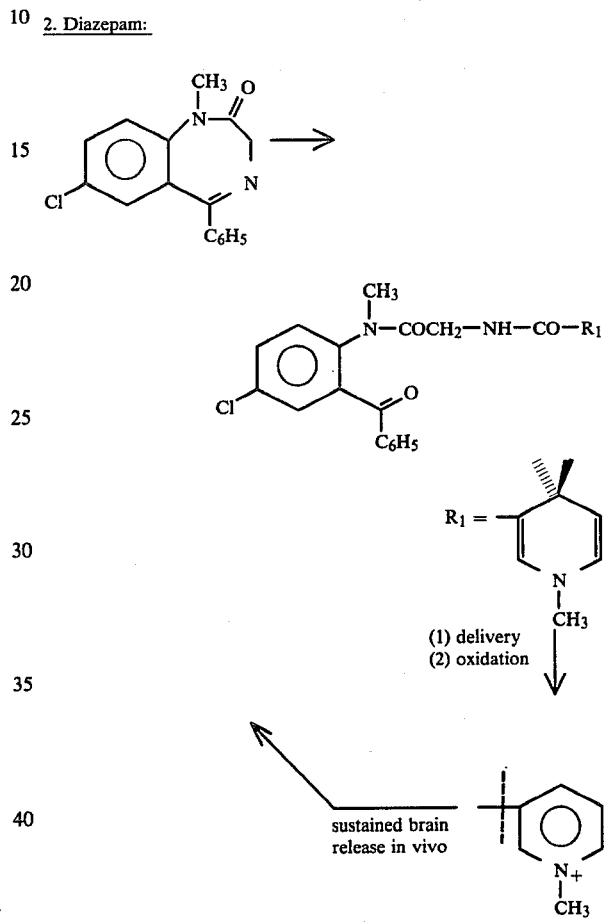

And in a preferred embodiment of the invention, there is provided the effective, selective and nontoxic treatment of epilepsy, based upon the mechanism illustrated in Scheme 1. Indeed, commencing from the "GABA-hypothesis" of epilepsy, the brain-specific, enhanced and sustained release of GABA (γ-aminobutyric acid) itself, and various other compounds either directly or indirectly affecting the concentrations of GABA in the brain, was circumscribed consistent herewith. Model compounds included carboxylic acids, most specifically valproic acid, as well as some of the GABA analogs which inhibit irreversibly the GABA-T, such as γ-vinyl and/or γ-acetylenic GABA. Using the aforesaid trigonnelline (N-methylnicotinic acid)-⇌dihydrotrigonelline system, for example, the selected compounds were effectively delivered per Scheme 1. Thus, representative target compounds were the dihydropyridine carrier-drug combinations 1 and the corresponding pyridinium carrier-drug species, for example, GABA and its esters:

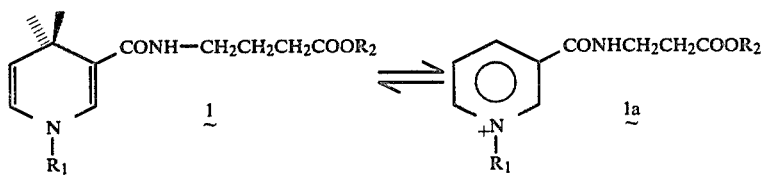

$R_1 = CH_3, C_3H_7$ or $CH_2C_6H_5$
$R_2 = H, C_2H_5, CH(CH_3)_2$, etc.

Related derivatives for γ-vinyl and γ-acetylenic GABA were:

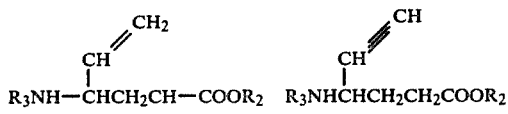

2 and 2a    3 and 3a $R_3 = $ 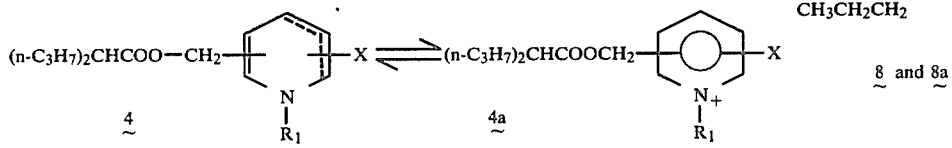

In the case of valproic acid, other alternatives were:

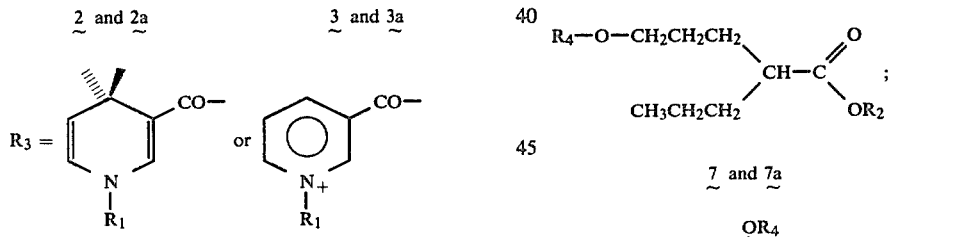

$X = H, CONH_2, CHNOR_2$, etc.

exemplified by the GABA case (5⇌5a) and valproic acid (6⇌6a):

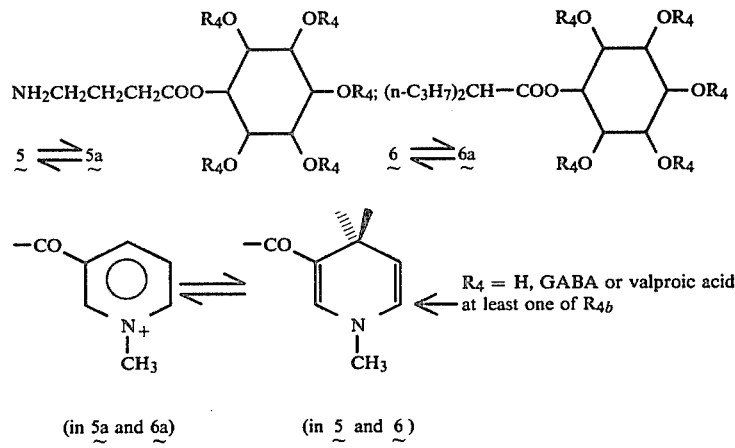

$R_4 = H$, GABA or valproic acid
← at least one of $R_{4b}$ (in 5a and 6a)    (in 5 and 6)

$R_4$ can be partially replaced by additional GABA or valproic acid, changing the carrier/drug ratio as necessary. Some of the valproic acid metabolites can be coupled with carriers of the redox type, via the various hydroxy groups formed during the oxidative degradation:

$$R_4-O-CH_2CH_2CH_2 \diagdown \atop CH_3CH_2CH_2 \diagup CH-C{\diagup O \atop \diagdown OR_2} ;$$

7 and 7a $$\begin{matrix} OR_4 \\ | \\ CH_3CH-CH_2 \\ \diagdown \\ \phantom{CH_3CH_2CH_2 \diagup} CH-COOR_2; \\ \diagup \\ CH_3CH_2CH_2 \end{matrix}$$

8 and 8a

In another embodiment of like delivery system, applicable for both the GABA and related compounds and for the carboxylic acids, or for any other drug species to be linked to such a carrier, either directly or indirectly, i.e., mediated by a carboxylic acid, e.g., succinic acid, or other linkage, provided was a mono- or poly-substituted nontoxic polyol (such as inositol or sugars) having the trigonelline⇌dihydrotrigonelline system and the compounds to be delivered linked to the same molecule as -continued

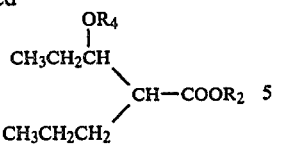

9 and 9a

Illustrative examples are the corresponding derivatives of the 5-(7)-, 4-(8)- and 3-(9)-hydroxy-2-n-propyl pentanoic derivatives. Additional carrier systems, such as the isoquinoline⇌dihydroisoquinoline system were also developed consistent herewith.

Moreover, based upon the observation that NADH content is significantly reduced in epileptic and like seizures, the use of the subject redox system (in reduced form) will bias the NAD⇌NADH balance towards NADH during the dihydro carrier→quaternary transformation. Also, the brain-specific delivery of small peptides consistent herewith, e.g., the enkephalins which have been found to initiate epileptic seizures, has led to the design of a variety of long lasting potent antagonists.

And the subject chemical delivery system is also useful for the delivery of other anticonvulsants in a sustained, brain-specific fashion, e.g., the benzodiazepines and hydantoins, and those compounds, like apomorphine, which are useful in the treatment of photosensitive epilepsy.

It will of course be appreciated in the immediately above regard that the drug treatment of epilepsy has always posed formidable problems. There are many different anticonvulsants available, some more specific for different types of seizures. Indeed, there exist a wide variety of opinions as to which is the most suitable drug for any particular type of seizure, and drug mixtures are typically employed. An inevitable result of the traditional therapy is the development of chronic toxicity, but such result is conspicuously avoided according to the present invention.

It too will be appreciated that the desired therapeutic effects of all antiepileptic agents investigated, as well as their undesired toxic effects, reflect a statistically significant correlation with the drug levels in plasma. This correlation is based upon a close relationship between the drug concentrations in plasma and brain tissue. Hence, a primary attribute of this invention is to enable attainment of high and sustained brain levels of the selected active agents, essentially against the plasma-brain concentration gradient and independent of the drug concentration in the blood.

GABA and related compounds are logical candidates. It has been shown that GABA neuron function is impaired in at least certain types of human epilepsy. Animal studies also showed that seizures are induced by reduction of GABA neuron function to a critical degree by (1) inhibition of GABA synthesis, (2) by blockade of GABA receptors or (3) inhibition of GABA-receptor mediated ionic events. In addition, enhancement of GABA synaptic activity (by direct receptor stimulation or by increasing GABA levels in the synapse) has a potent and wide-spectrum anticonvulsant effect. These findings foreshadowed that an enhanced and sustained GABA brain delivery or a brain-specific delivery in a sustained manner of a good GABA-agonist would be efficacious in different forms of epilepsy. It is well known that GABA itself, when administered systematically, does not penetrate the normal blood-brain barrier to any significant extent. Among the potential sites at which drugs may act to influence GABA-mediated synaptic function, the first target is to effect the BBB transfer of GABA via a redox delivery system. The second main target is to effect the catabolism of GABA. This invention, accordingly, specifically provides for the efficacious delivery of the GABA-T inhibitors, γ-vinyl and γ-acetylene-GABA, but the delivery of valproic acid, specifically to the brain and without requiring high circulating blood levels, is also envisaged. In order to achieve the required activity, sodium valproate must have a relatively high, 50-100 μg/ml, level in the blood. The value of valproic acid is well established in most types of epilepsy. It is evident that valproic acid produces significant increases in both brain and synaptosomal GABA concentrations. Valproic acid itself undergoes extensive metabolism.

In capsule summary, the present invention provides for the significantly improved treatment of epilepsy, and concomitant reduction in toxicity of a number of antiepileptic drug species currently in use. And made available to the brain is a variety of important compounds, such as GABA and a wealth of GABA-ergic agents.

Thus, provided hereby is a flexible arsenal of dihydropyridine⇌pyridinium salt redox carriers for the site-specific/sustained delivery of virtually any centrally acting drug species to the brain. Moreover, any dihydropyridine/pyridinium salt redox carrier entity is contemplated and intended hereby generically, and any such carrier moiety need not be, and is not derivatized with a drug release rate controlling substituent critically tailored to meet, or be coordinated with, the chemical nature and delivery requirements of the particular drug species sought be be preferentially administered to the brain. As utilized herein, the term "carrier" is to be understood as connoting just such a non-derivatized, non-drug/carrier coordinated entity, for consistent herewith it is the "carrier" entity itself and not the nature of any activity or release rate controlling/modifying substituent which is responsible for providing the desired brain-specific result illustrated in the Scheme 1.

Additional examples of such redox carriers include the quaternary pyridinium alcohols (1), the analog isoquinoline acid and alcohol systems (2), and multi-charged delivery forms, exemplified by structure 3 (D represents drug, Z a covalent link) and obviously the corresponding dihydro forms.

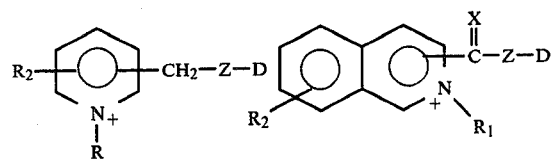

3

Yet other redox carriers include those comprising an acidic chain directly linked to the heterocyclic nitrogen, in quaternary or tertiary amine form. Also the hydroxide type carriers, e.g., the glucosamine analog indicated below. Representative are:

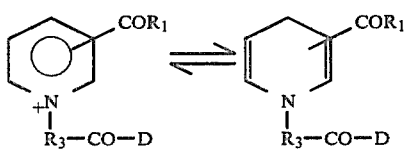

(a)

$R_1 = NH_2$; $OR_2$ and the like $R_2$ = alcohol residue $R_3 = (CH_2)_n$ n = 1–10 or $C_1$–$C_{12}$ branched alkyl, arylalkyl, and the like D = drug—$NH_2$ or —OH;

Preparation:

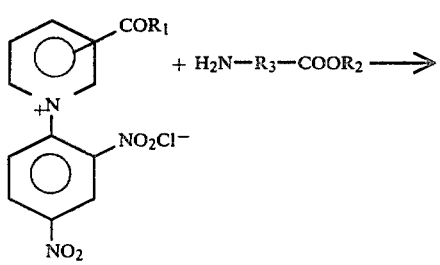

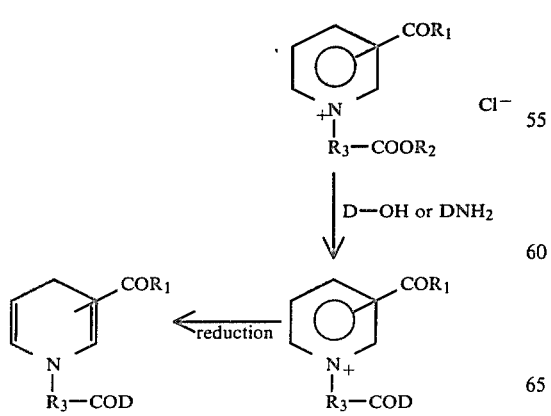

Method of: H. Lattre et al., Annalen, 579, 123 (1953).

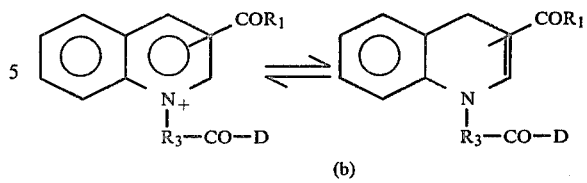

(b)

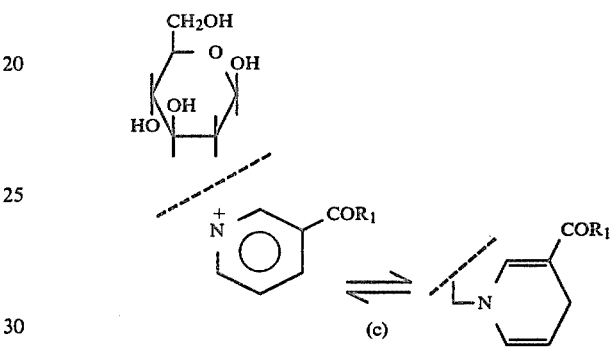

(c)

And all of the aforesaid carriers are well suited for the brain-specific delivery of any of the centrally or brain acting drug species, not the least of which being the anticancer and antitumor agents, such as:

Methotrexate:

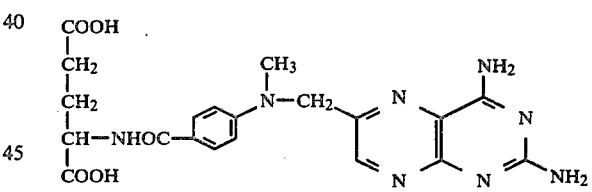

using the acids and alcoholic carriers, such as the inositol trigonellinates or the glucosamine analog.

Podophyllotoxin derivatives:

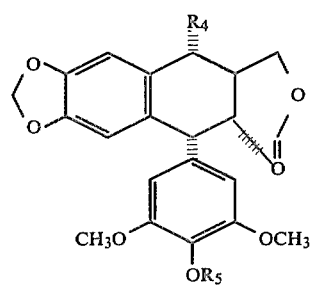

$R_5$ = H or $CH_3$ $R_4$ = OH—podophyllotoxin

-continued

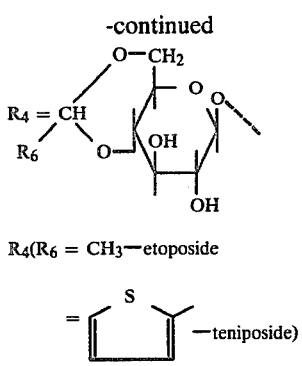

R₄(R₆ = CH₃—etoposide

= 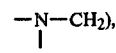 —teniposide)

Derivatizing R₄—OH or OH groups in glycosidic portions in R₄ with acidic type redox carriers.

Suitable nontoxic pharmaceutically acceptable carriers for use with the topic compounds [D-DHC], e.g., those less toxic than the target drug species themselves, will be apparent to those skilled in this art. Compare, for example, *Remington's Pharmaceutical Sciences,* 4th Edition (1970). Obviously, the choice of suitable carriers will depend upon the exact nature of the particular dosage form selected, as well as upon the identity of the active drug species [D]. The therapeutic dosage ranges for administration of the compounds according to this invention will generally be the same as, or less than those characteristically used in this art for administration of the known drug species [D], per se. Naturally, such therapeutic dosage ranges will vary with the size of the patient, the condition for which the [D-DHC] compound is administered, the particular dosage form employed, and the like. The quantity of given dosage form needed to deliver the desired dose of [D] will of course depend upon the concentration of [D-DHC] in any given pharmaceutical composition/dosage form thereof.

In order to further illustrate the present invention and the advantages thereof, the following specific examples are given, it being understood that same are intended only as illustrative and in nowise limitative.

In the examples immediately to follow, all melting points were taken on a Mel-Temp apparatus and are not corrected. Elemental analyses were performed at Atlantic Microlab, Inc., Atlanta, Ga. Infrared spectra were determined using a Beckman Acculab 1 double-beam recording spectrophotometer. NMR spectra were determined by means of a Varian T60A spectrometer. All chemical shifts reported are in δ units (parts per million) relative to tetramethyl silane. Ultraviolet absorbance spectra were determined using a Cary Model 219 spectrophotometer. HPLC analysis were performed on Waters Associates Liquid chromatograph with Model 6000A solvent delivery system, Model U6K injector and Model 440 absorbance detector. And in all cases where Anal. C, H, N is indicated, the elementary analysis of the compound was found within ±0.4 of the calculated value.

EXAMPLE 1

Preparation of N-(β-Phenethyl)nicotinamide (compound 1)

To 10.25 g (0.083 mol) of nicotinic acid, 27.5 ml of thionyl chloride was gradually added. The mixture was stirred at room temperature for 10 min and then refluxed while stirring for 2 hrs. Excess thionyl chloride was then distilled off under reduced pressure. Dry benzene (over sodium, 50 ml) was added and then distilled off under reduced pressure (to get rid of traces of $SOCl_2$). A white crystalline acid chloride hydrochloride was left, which was used as such for the preparation of amides.

To the solid acid chloride hydrochloride, 150 ml of dry and freshly distilled pyridine was added. To the stirred mixture, 10.45 ml (0.083 mol) of phenethylamine was dropped over 15 min. The mixture was then heated on a water bath while stirring for 2 hrs. Pyridine was distilled off on rotavap. The brown oily residue was poured onto crushed ice. The cream-white solid separated was filtered by suction, washed with cold water and dried in vacuum; yield 13.3 g (70%), m.p. 79°–80°; ir (KBr) 3320 (NH) and 1630 cm$^{-1}$ (C=O), NMR (CDCl₃) δ8.66 (bs, 1H, C₄ pyridine proton), 8.46 (bd, 1H, C₆ pyridine proton), 8.0–7.6 (m, 1H, C₄ pyridine proton), 7.33–6.90 (bs, 6H, C₆H₅+C₅ pyridine proton), 7.0–6.57 (hump, 1H, CONH), 3.73 (q, 2H, $$-\underset{|}{N}-CH_2),$$

2.97 (t, 2H, CH₂—φ).

Anal. (C₁₄H₁₄N₂O) C, H, N.

EXAMPLE 2

Preparation of 1-Benzyl-3-(N-β-phenethyl)carbamoyl pyridinium bromide (compound 2)

To a solution of 2.26 g (0.01 mol) of N-(β-phenethyl) nicotinamide (1) in 5 ml of methanol, 1.4 ml (0.0114 mol) of benzyl bromide was added. The mixture was refluxed for 3 hrs. Methanol was distilled off on rotavap. The yellow, oily residue left was scratched when it suddenly solidified into buff, gritty solid. Crystallized from acetone/ether, yield 3.7 g (95%), m.p. 142°–144°, U.V. max (buffer pH 7.4) 210 and 260 nm; ir (KBr) 3180 (NH) and 1670 cm$^{-1}$(C=O). NMR (CDCl₃/DMSO-d₆) δ10.26 (bs, 1H, C₂ pyridine proton), 9.53–8.90 (m, 2H, C₆ and C₄ pyridine protons), 8.16–7.13 (m, 12H, 2C₆H₅+CONH+C₅ pyridine protons), 6.13 (s, 2H, $$-\overset{+}{\underset{|}{N}}-CH_2),$$

3.96–3.50 (m, 2H, —N—CH₂), 3.26–2.83 (m, 2H, CH₂—φ). Anal. (C₂₁H₂₁BrN₂O) C, H, N.

EXAMPLE 3

Preparation of 1-Methyl-3-(N-β-phenethyl)carbamoyl iodide (compound 3)

To a solution of 2.26 g (0.01 mol) of N-(β-phenethyl) nicotinamide in 5 ml of methanol, 1.3 ml (0.02 mol) of methyl iodide was added. The mixture was refluxed for 3 hrs. Methanol was distilled off on rotavap and the yellow, oily residue was cooled and scratched when a yellow gritty solid was obtained. Crystallized from acetone, yield 3.5 g (95%), m.p. 134°–136°, U.V. max (buffer pH 7.4) 210, 225 and 266 nm. Ir (KBr) 3240 (NH) and 1665 cm$^{-1}$ (C=O). NMR (CDCl₃/DMSO-d₆) δ9.63 (s, 1H, C₂ pyridine proton), 9.4–8.9 (m, 2H, C₄ and C₆ pyridine protons), 8.32–8.06 (m, 1H, C₅ pyridine proton), 4.6 (s, 3H, —N⁺—CH₃), 3.9–3.46 (m, 2H, —N—CH$_2$), 3.2-2.8 (m, 2H, CH$_2$—$\phi$). Anal. (C$_{15}$H$_{17}$IN$_2$O) C, H, N.

EXAMPLE 4

Preparation of 1-Benzyl-3-(N-$\beta$-phenethyl)carbamoyl-1,4-dihydropyridine (compound 4)

To a solution of 3.97 g (0.01 mol) of compound 2 in 200 ml of deaerated water, 5.0 g (0.06 mol) of sodium bicarbonate and 200 ml of ether were added. The mixture was stirred in an ice bath and 7.1 g (0.04 mole) of sodium dithionite were added gradually over a period of 5 min. The mixture was stirred for 3 hrs under nitrogen. The ether layer was then separated, washed with water, dried with Na$_2$SO$_4$ and distilled under vacuo. Yield 2.3 g (72%) of bright yellow, viscous oil was obtained which gave positive test for dihydropyridine with alcoholic silver nitrate solution. U.V. max (buffer pH 7.4) 210 and 355 nm. NMR (CDCl$_3$) $\delta$ two overlapping singlets at 7.2 (10H, 2C$_6$H$_5$), 7.1 (bs, 1H, C$_2$ pyridine proton), 5.68 (doublet of doublets, 1H, J=8 and 2 cps, C$_6$ pyridine proton), 6.4-5.0 (hump, 1H, CONH), 4.84-4.60 (m, 1H, C$_5$ pyridine proton), 4.35 (s, 2H, N—CH$_2$), 3.5 (q, 2H, J-7.0,

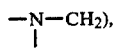

3.0 (bs, 2H, C$_4$ pyridine proton) and 2.8 (t, 2H, J=7.0, CH$_2$—$\phi$).

EXAMPLE 5

Preparation of 1-Methyl-3-(N-$\beta$-phenethyl)carbamoyl-1,4-dihydropyridine (compound 5)

By the similar method described above, compound 3 (3.68 g, 0.01 mol) was reduced using sodium dithionite (7.1 g, 0.04 mol) and sodium bicarbonate (5.0 g, 0.06 mol). Yield 1.8 g (76%) of bright yellow, viscous oil which reduced alcoholic silver nitrate solution. U.V. max (buffer pH 7.4) 210, 290 and 360 nm; NMR (CDCl$_3$) $\delta$7.2 (s, 5H, C$_6$H$_5$), 6.9 (bs, 1H, C$_2$ pyridine proton), 5.6 (doublet of doublets, 1H, J=8, 2 cps, C$_6$ pyridine proton), 5.3-5.1 (hump, 1H, CONH), 4.5-4.7 (m, 1H, C$_5$ pyridine protons+N—CH$_3$+CH$_2$—$\phi$). Anal. (C$_{15}$H$_{18}$N$_2$O) C, H, N.

EXAMPLE 6

Preparation of Diethyl-3,5-pyridine dicarboxylate (compound 6)

To suspension of 8.35 g (0.05 mol) of 3,5-pyridine dicarboxylic acid in 30 ml of absolute ethanol, 10 ml of concentrated sulfuric acid was dropped while stirring. The mixture was then refluxed on a water bath for 5 hrs and poured onto crushed ice. The solution was then made alkaline by the addition of solid KHCO$_3$ in small amounts. A white solid separated which was filtered, washed with water and dried. M.p. 42°-44°. The motther liquid was extracted with CH$_2$Cl$_2$ when another crop of the diester was obtained. The overall yield of the crude ester was 9.1 g (82%) of sufficient purity for the examples to follow. The NMR (CDCl$_3$) $\delta$9.62 (d, 2H, J-2 Hz, C$_2$ and C$_6$ pyridine protons), 8.76 (t, 1H, J=2 Hz, C$_4$ pyridine proton), 4.43 (q, 4H, J=7 Hz, 2 OCH$_2$), 1.41 (t, 6H, J=7 Hz, 2 CH$_3$).

EXAMPLE 7

Preparation of 5-Carboethoxy-3-pyridine carboxylic acid (compound 7)

To a solution of 10 g (0.045 mol) of compound 6 in 75 ml of ethyl alcohol, 25 ml of 2N alcoholic KOH was added while stirring. Stirring was continued for ½ hr at room temperature. To the mixture 12.5 ml of 4N HCl was added while stirring. The solid separated was filtered and washed with alcohol. The combined filtrate and washings were distilled on rotovap and the residue was washed with water, filtered and crystallized from ethanol. Yield 7.5 g (86%), m.p. 180°-182°, NMR (CDCl$_3$/DMSO-d$_6$) $\delta$10.56 (bs, 1H, COOH), 9.26 (d, 2H, J=2 Hz, C$_2$ and C$_6$ pyridine protons), 8.75 (t, 1H, J=2 Hz, C$_4$ pyridine protons), 4.4 (q, 2H, J=7 Hz, O—CH$_2$), 1.42 (t, 3H, J=7 Hz, CH$_3$).

EXAMPLE 8

Preparation of 5-Carboethoxy-3-(N-$\beta$-phenethyl)carbamoyl pyridine (compound 8)

To 10 g (0.05 mol) of compound 7, 30 ml of thionyl chloride was added and the mixture was warmed on a water bath while stirring until clear ($\approx$3 hrs). Excess thionyl chloride was distilled under vacuum. The residue was cooled to room temperature and 50 ml of sodium-dry benzene was added. The solution was cooled in an ice bath and a solution of 6.2 g (0.051 mol) of phenethylamine and 4 ml of pyridine in 50 ml of dry benzene was dropped while stirring over 1 hr and the mixture was left overnight at room temperature. The mixture was then washed with water until free from Cl$^-$ (tested by AgNO$_3$TS). The organic layer was dried with Na$_2$SO$_4$ and distilled. The residue was crystallized from ether/pet. ether mixture. Yield 9.0 g (67%), m.p. 159°-161°; ir (KBr) 3300 (NH), 1725 (ester CO) and 1650 cm$^{-1}$ (amide CO), NMR (CDCl$_3$) 9.13-8.96 (two doublets, 2H, J=2 Hz, C$_2$ and C$_6$ pyridine protons), 8.53 (t, 1H, J=2 Hz, C$_4$ pyridine proton), 7.16 (s, 6H, C$_6$H$_5$+CONH), 4.36 (q, 2H, J=7 Hz, OCH$_2$), 3.4 (q, 2H, J=7 Hz, N—CH$_2$), 2.9 (5, 2H, J=7 Hz, CH$_2$—$\phi$), 1.33 (t, 3H, J=7 Hz, CH$_3$). Anal. (C$_{17}$H$_{18}$N$_2$O$_3$) C, H, N.

EXAMPLE 9

Preparation of 5-Carboethoxy-1-methyl-3-(N-$\beta$-phenethyl)carbamoyl pyridinium iodide (compound 9)

To a solution of 2.9 g (0.01 mol) of compound 8 in 5 ml of acetone, 3 ml of methyl iodide was added. The mixture was refluxed while stirring for 8 hrs and then left overnight. The yellow crystalline solid precipitated was filtered, washed with acetone, dried and crystallized from acetone. Weight 3.5 g (82%), m.p. 168°-170°, ir (KBr) 3250 (NH), 1725 (ester CO) and 1670 cm$^{-1}$ (amide CO), U.V. max (buffer pH 7.4) 268 (weak plateau) and 268 nm ($\epsilon$=53, 667), NMR (DMSO-d$_6$) $\delta$9.53 (bs, 2H, C$_2$ and C$_6$ pyridine protons), 9.33-9.10 (m, 1H, C$_4$ pyridine proton), 7.16 (s, 5H, C$_6$H$_5$), 4.63-4.26 (complex multiplet, 5H,

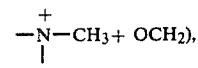

3.56 (q, 2H, J=6 Hz,

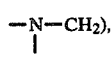

2.90 (t, 2H, J=6, CH$_2$—$\phi$), 1.4 (t, 3H, J=7 Hz, CH$_3$). Anal. (C$_{18}$H$_{21}$IN$_2$O$_3$) C, H, N.

EXAMPLE 10

Preparation of 5-Carboethoxy-1-methyl-3-(N-$\beta$-phenethyl)carbamoyl-1,4-dihydropyridine (compound 10)

This compound was prepared following the same procedure as for compound 4 using 1.0 g (0.002 mol) of 9, 1.0 g (0.012 mol) sodium bicarbonate and 1.42 g (0.008 mol) sodium dithionite. Yield, 0.60 g (84%) of orange-yellow viscous oil which reduced alcoholic silver nitrate, but very slowly. U.V. max (buffer pH 7.4) 205 and 390 nm. NMR (CDCl$_3$) 7.33 (s, 5H, C$_6$H$_5$), 7.0 (s, 2H, C$_2$ and C$_6$ pyridine protons), 5.8–5.3 (hump, 1H, CONH), 4.2 (q, 2H, J=7, O—CH$_2$), 3.66 (q, 2H, J=7 Hz,

—N—CH$_2$),
|

3.16 (bs, 2H, C$_4$ pyridine proton), 3.0 (q, 2H, J=7, CH$_2$—$\phi$), 1.4 (t, 3H, J=7, CH$_3$).

EXAMPLE 11

Preparation of 3,4-Di(N-$\beta$-phenethyl)carbamyl pyridine (compound 11)

To a solution of 2.53 g (0.01 mol) of diethyl, 3,5-pyridine dicarboxylate in 10 ml of methanol, 3.0 g (0.025 mol) of phenethylamine was added. The mixture was refluxed overnight and then distilled. The residue was washed with very dilute HCl solution and water, dried and crystallized form ethanol. Yield 2.9 g (80%), m.p. 189°–190°. NMR (CDCl$_3$) $\delta$9.00 (d, J=2 Hz, 2H, 2,6-dipyridyl), 8.33 (t, J=2, 1H, 4-pyridyl), 7.30 (s, 10H, 2 C$_6$H$_5$), 6.93–6.40 (hump, 2H, 2 COHN), 3.83 (q, J=7, 4H, 2 —N—CH$_2$), 3.00 (t, J=7, 4H, 2 —CH$_2$—$\phi$). Anal. (C$_{23}$H$_{23}$N$_3$O$_2$) C, H, N.

EXAMPLE 12

Preparation of 1-Methyl-3,5-di(N-$\beta$-phenethyl)carbamoyl pyridinium iodide (compound 12)

To a solution of 2.0 g (5.3 mmol) of the diamide 10 in 10 ml of acetone, 2 ml of methyl iodide was added and the mixture was refluxed for 24 hrs. The yellow crystalline solid separated was filtered, washed with acetone and dried. Weight 1.4 g (51%), m.p. 186°–188°. U.V. spectrum of a solution in phosphate buffer 7.4 showed a plateau at 275 nm, a shoulder at 225 nm and a sharp peak at 203 nm ($\epsilon$=67,356). Ir (KBr) 3240 (NH), 1665 and 1650 cm$^{-1}$ (twin band, C=O). NMR (CDCl$_3$/D$_2$O) $\delta$9.35 (d, 2H, J=2, C$_2$ and C$_6$ pyridine protons), 8.56 (d, 1H, J=2 Hz, C$_4$ pyridine proton), &0.20 (s, 10H, 2 C$_6$H$_5$), 4.56 (s, 3H,

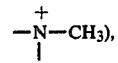

3.66 (t, 4H, J=7 Hz, 2 —N—CH$_2$), 2.96 (t, 4H, J=7 Hz, 2 CH$_2$—$\phi$). Anal. (C$_{24}$H$_{26}$IN$_3$O$_2$).

EXAMPLE 13

Preparation of 1-Methyl-3,5-di(N-$\beta$-phenethyl)carbamoyl-1,4-dihydropyridine (compound 13)

This compound was prepared following the same procedure as for compound 4, using 1 g (0.002 mol) of 12, 1.0 g (0.012 mol) sodium bicarbonate and 1.4 g (0.008 mol) sodium dithionite. Yield 0.65 g (86%) of orange-yellow semisolid which could not be crystallized. Its alcoholic solution shows a slow reduction to alcoholic silver nitrate solution. U.V. max (buffer pH 7.4) 388 and 210 nm. NMR (CDCl$_3$) 7.13 (s, 5H, C$_6$H$_5$), 6.76 (s, 1H, C$_2$ pyridine protons), 3.51 (q, 4H, J=7 Hz, 2

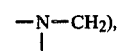

3.06–2.60 (m, 9H, O—CH$_2$+C$_4$ pyridine proton+-N—CH$_3$).

EXAMPLE 14

Preparation of N-Nicotinoyldopamine (compound 14)

To a pyridine solution containing 11.7 g (0.05 mol) dopamine hydrobromide and 6.15 g (0.05 mol) nicotinic acid at 0°, there was added 10.3 g (0.05 mol) dicyclohexylcarbodiimide (DCC). The reaction mixture was stirred at room temperature for 24 hrs and the formed dicyclohexylurea was removed by filtration. The pyridine was removed by distillation in vacuo and the residue was crystallized in water at 0°. The product was isolated by filtration and dried over phosphorous pentoxide. Recrystallization from isopropanol gave 9.0 g (0.035 mol), 70%, N-nicotinoyldopamine, m.p. 156°–162°; aqueous solution of the compound gave green color with Fe$^{-3}$ and reduced AgNO$_3$TS, ir (KBr) 3300, 2960, 1725, 1630, 1590, 1520, 1430, 1290, 1190, 1115, 740 and 710 cm$^{-1}$; pmr (d$_6$-DMSO) $\delta$9.25–6.25 (m, 7H), 3.3 (m, 2H) and 2.65 (m, 2H) ppm. Anal. (C$_{14}$H$_{14}$N$_2$O$_3$) C, H, N.

EXAMPLE 15

Preparation of 3-{N-[$\beta$-(3,4-Diacetoxyphenyl)ethyl]}carbamoyl pyridine (compound 15)

To an ice cold suspension of 2.06 g (8 mmol) finely powdered nicotinoyldopamine in 50 ml of chloroform, 1.56 g (10 mmol) of acetylchloride was dropped while stirring. The mixture was refluxed for 3 hrs, then filtered. The filtrate was washed with water until the washing did not give test for chloride ions with AgNO$_3$ T.S. Chloroform was distilled on rotavap and the residue was crystallized from ether/pet. ether. Yield 2.2 g (81%), m.p. NMR (CDCl$_3$) 8.90 (bs, 1H, C$_2$ pyridine proton), 8.56 (bd, 1H, C$_6$ pyridine proton), 8.16–7.83 (m, 1H, C$_4$ pyridine proton), 7.36–7.03 (m, 5H, C$_6$H$_3$+C$_5$ pyridine proton+NH), 3.60 (q, 2H, J=7 Hz,

2.90 (t, 2H, J=7 Hz, —CH$_2$).

EXAMPLE 16

Preparation of 3-{N-[β-(3,4-Dipivalyloxyphenyl)ethyl]}carbamoyl pyridine (compound 16)

To a suspension of 5.16 g (0.02 mol) finely powdered nicotinoyldopamine in 100 ml of chloroform, 7.23 g (0.06 mol) trimethylacetyl chloride was dropped while stirring. The mixture was refluxed for 6 hrs and then filtered. The filtrate was washed with water until free of chloride ions, then washed once with 5% solution of NaHCO$_3$ then with water. Chloroform was distilled off on rotavap and the residue was chromatographed using silica gel G column and 2% methanol in chloroform as the elution solvent. The first fraction was collected, evaporated and the residue was crystallized from ether/pet. ether. Yield 6.2 g (78%) of white crystalline solid, m.p. 112°–114° C., PMR (CDCl$_3$) 9.06 (bs, 1H, C$_2$ pyridine proton), 8.73 (bd, 1H, C$_6$ pyridine proton), 8.30–8.13 (m, 1H, C$_4$ pyridine proton), 7.46–7.10 (m, 5H, C$_6$H$_3$+C$_5$ pyridine proton+CONH), 3.66 (q, 2H, J=6.25 Hz,

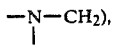

3.0 (t, 2H, J=6.5 Hz, —CH$_2$), 1.41 (s, 18H, 2—C—(CH$_3$)$_3$). Anal. (C$_{24}$H$_{30}$N$_2$O$_5$) C, H, N.

EXAMPLE 17

Preparation of 1-Methyl-3-{N-[β-(3,4-dihydroxyphenyl)ethyl]}carbamoyl pyridinium iodide (compound 17)

To a solution of 1.26 g (5 mmol) of nicotinoyldopamine, (14) in 10 ml of acetone, 1.41 g (10 mmol) of methyl iodide was added and the mixture was refluxed while stirring for 6 hrs. Acetone was distilled off and the residue was crystallized from methanol/ether. Yield, 1.7 g (87%), m.p. 155°–157° (dec.). Aqueous solution gives green color with Fe$^{+3}$, PMR (D$_2$O) δ9.30–8.28 (ms, 4H, C$_5$H$_4$N$^+$), 7.00 (bs, 3H, C$_6$H$_3$), 4.60 (s, 3H,

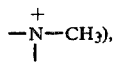

3.80 (t, 2H, J=7 Hz, —N—CH$_2$), 2.93 (t, 2H, J=7 Hz, CH$_2$). Anal. (C$_{15}$H$_{17}$IN$_2$O$_3$) C, H, N.

EXAMPLE 18

Preparation of 1-Methyl-3-{N-[β-(3,4-diacetoxyphenyl)ethyl]}carbamoyl pyridinium iodide (compound 18)

To a solution of 1.41 g (5 mmol) of compound 2 in 10 ml of acetone, 1.41 g (10 mmol) of methyliodide was added and the mixture was refluxed overnight while stirring. The acetone solution was then decanted from the insoluble, oily residue. Ether was added to the acetone solution and the solid separated was crystallized from acetone/ether. Yield, 1.9 g (78%) of yellow, crystalline needles, m.p. 171°–173°. U.V. (methanol) 215 and 265 nm, PMR (D$_2$O) δ8.86–7.63 (ms, 4H, C$_5$H$_4$N$^+$), 6.66 (bs, 3H, C$_6$H$_3$), 4.4 (s, 3H,

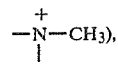

3.50 (t, 2H,

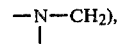

3.03 (t, 2H, CH$_2$), 2.21 (bs, 6H, 2 COCH$_3$). Anal. (C$_{19}$H$_{21}$IN$_2$O$_3$) C, H, N.

EXAMPLE 19

Preparation of 1-Methyl-3-{N-[β-(3,4-dipivalyloxyphenyl)ethyl]}carbamoyl pyridinium iodide (compound 19)

To a solution of 5.0 g (11.7 mmol) of compound 3 in 20 ml of acetone, 3.3 g (23.4 mmol) of methyl iodide was added and the mixture was refluxed while stirring for 6 hrs, then cooled. An orange, crystalline solid separated which was filtered, washed with ether and then crystallized from acetone/ether. Yield, 5.6 g (85%), m.p. 163°–165°. U.V. (buffer, pH 7.4) 270 and 215 nm. PMR (DMSO-d$_6$) 7.68–7.06 (ms, 7H, C$_5$H$_4$N$^+$+C$_6$H$_3$+HN), 4.56 (s, 3H, —N$^+$—CH$_3$), 3.42 (q, 2H, J=7 Hz, —N—CH$_2$), 3.19 (t, 2H, J=7 Hz, CH$_2$), 1.32 (s, 18H, 2 —C(CH$_3$)$_3$). Anal. (C$_{25}$H$_{33}$IN$_2$O$_5$) C, H, N.

EXAMPLE 20

Preparation of 1-Methyl-3-{N-[β-(3,4-dihydroxyphenyl)ethyl]}carbamoyl-1,4-dihydropyridine (compound 20)

To an ice cold solution of 1.0 g (2.5 mmol) of compound 4 in 200 ml of deaerated water, 1.26 g (15 mmol) sodium bicarbonate was added. Nitrogen was bubbled into the mixture and 1.75 g (10 mmol) of sodium dithionite was added gradually to the mixture while stirring. Stirring was continued for 1 hr and the mixture was then extracted twice with 50 ml of ether. The ether extract was washed with water, dried with anhydrous Na$_2$SO$_4$ and evaporated on rotavap. Yield, 0.36 g (54%) of a yellow, viscous oil which gave green color with ferric chloride test and reduced alcoholic AgNO$_3$ instantly. U.V. (CH$_3$OH) 220 and 360 nm.

EXAMPLE 21

Preparation of 1-Methyl-3-{N-[β-(3,4-diacetoxyphenyl)ethyl]}carbamoyl-1,4-dihydropyridine (compound 21)

To an ice cold solution of 1.4 g (3 mmol) of compound 5 in 200 ml of deaerated water, 1.5 g (18 mmol) of sodium bicarbonate was added. A stream of N$_2$ was bubbled into the mixture and 2.1 g (12 mmol) of sodium dithionite was gradually added while stirring. Stirring was continued for 30 min and then the mixture was extracted with ethyl acetate. The extract was washed with water, dried with anhydrous Na$_2$SO$_4$ and evaporated on rotavap. The yellowish semisolid mass remaining gave a faint green color with ferric chloride test indicating partial hydrolysis of the ester functions. It reduced alcoholic silver nitrate instantly. U.V. (CH₃OH) 220, 273 and 355 nm, PMR (CDCl₃/D₂O) δ7.13–6.80 (ms, 4H, C₆H₃+C₂ dihydropyridine proton), 5.53 (doublet of doublets, 1H, C₆ dihydropyridine proton), 4.63–4.46 (m, 1H, C₅ dihydropyridine proton), 3.33 (t, 2H, J=6.5 Hz,

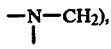

3.06–2.66 (m, 7H,

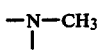

+C₄ dihydropyridine protons+—C₆H₂).

EXAMPLE 22

Preparation of 1-Methyl-2-{N-[β-3,4-dipivalyloxyphenyl)ethyl]}carbamoyl-1,4-dihydropyridine (compound 22)

To a cold mixture of 2.0 g (3.5 mmol) of compound 6, 200 ml of deaerated water and 100 ml of ethyl acetate, 1.14 g (14 mmol) of sodium bicarbonate and 2.43 g (14 mmol) of sodium dithionite were added. The mixture was stirred under N₂ for 20 min. The ethyl acetate layer was separated and the aqueous layer was reextracted with 100 ml of ethyl acetate. The combined ethyl acetate was washed with cold deaerated water, dried over anhydrous Na₂SO₄ and distilled on rotavap. The viscous, yellow oily residue was dissolved in 5 ml of acetone, filtered through folded filter paper under N₂ atmosphere and then evaporated under reduced pressure. The solid residue was dried under vacuum over P₂O₅ in N₂ atmosphere. It reduced alcoholic AgNO₃ instantaneously and gave no color with FeCl₃ test. Yield, 1.3 g (83%), m.p. 45°–48°. U.V. (CH₃OH) 210 and 355 nm, PMR (CDCl₃) δ 7.04–6.92 (m, 4H, C₆H₃+C₂ dihydropyridine proton), 4.81 (bs, 1H, CONH), 4.60–4.51 (m, 1H, C₅ dihydropyridine proton), 3.53 (q, 2H, J=6.3 Hz,

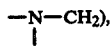

2.36 (bs, 2H, C₄ dihydropyridine proton), 2.91 (s, 3H, N—CH₃), 2.79 (t, 2H, J=6.3 Hz, CH₂), 1.33 (s, 18H, 2 CO—C(CH₃)₂).

EXAMPLE 23

Preparation of N-Nicotinoyltyramine (compound 23)

To an ice cold suspension of 3.69 g (0.03 mol) nicotinic acid in a solution of 5.2 g (0.03 mol) tyramine hydrochloride in 100 ml of pyridine, 6.18 g (0.03 mol) of dichlorohexylcarbodiimide (DCC) was gradually added while stirring. Stirring was continued at room temperature for 24 hrs and the formed dichclohexylurea was removed by filtration. The pyridine was removed by distillation in vacuo and the residue was triturated with cold water, filtered and crystallized from 50% aqueous methanol. Yield, 6.25 g (86%), m.p. 179°–181° C. PMR (DMSO-d₆/D₂O)δ 9.0–8.66 (m, 2H, C₂ and C₆ pyridine protons), 8.33–8.10 (m, 1H, C₄ pyridine proton), 7.66–7.46 (m, 1H, C₅ pyridine proton), 7.23–6.70 (m, rH, C₆H₄), 3.56 (t, 2H,

2.90 (t, 2H, CH₂). Anal. (C₁₄H₁₄N₂O₂) C, H, N.

EXAMPLE 24

Preparation of 3-{N-[β-(4-pivalyloxyphenyl)ethyl]}carbamoyl pyridine (compound 24)

To an ice cold suspension of 4.84 g (0.02 mol) N-nicotinoyl tyramine in 100 ml chloroform, 3.6 g (0.03 mol) of trimethylacetyl chloride was dropped while stirring. The mixture was refluxed overnight and the non-reacted nicotinoyl dopamine was filtered off. The filtrate was washed with water until free from chloride ions, washed once with 5% solution of NaHCO₃ and then with water. Chloroform was evaporated on rotavap and the residue was crystallized from ether/pet. ether. Yield 3.9 g (60%), m.p. 80°–82°. PMR (CDCl₃)δ 8.66–6.93 (m, 8H, C₅H₄N+C₆H₄), 3.56 (q, 2H, J=7 Hz,

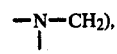

2.86 (t, 2H, J=7 Hz, CH₂), 1.33 (s, 9H, C—(CH₃)₃).

EXAMPLE 25

Preparation of 1-Methyl-3-{N-[β-(4-hydroxyphenyl)ethyl]}carbamoyl pyridinium iodide (compound 25)

To a solution of 1.21 g (5 mmol) of nicotinyoltyramine in 10 ml of acetone, 1.41 g (10 mmol) of methyl iodide was added and the mixture was refluxed while stirring for 6 hrs. The fine, yellow solid separated was filtered and crystallized from methanol ether. Yield, 1.78 g (93%), m.p. 208°–210° C. PMR (DMSO-d₆/D₂O)δ 9.23–8.26 (m, 4H, C₅H₄N+), 7.33–6.83 (m, 4H, C₆H₄), 4.50 (s, 3H,

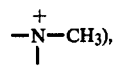

3.70 (t, J=7 Hz, 2H,

2.93 (t, J=7 Hz, 2H, CH₂).

EXAMPLE 26

Preparation of 1-Methyl-3-{N-[β-(4-pivalyloxyphenyl)ethyl]}carbamoyl pyridinium iodide (compound 26)

To a solution of 1.63 g (5 mmol) of compound 24 in 10 ml of acetone, 1.41 g (10 mmol) methyl iodide was added and the mixture was refluxed overnight while stirring. The acetone layer was separated by decantation and the yellowish, oily residue was crystallized from methanol/ether. Yield, 1.94 g (83%), m.p. 155°-157° C. PMR (D$_2$O)δ 9.16-8.00 (m, 4H, C$_5$H$_4$N$^+$), 7.33-6.83 (m, 4H, C$_6$H$_4$), 4.40 (s, 3H, N$^+$—CH$_3$), 3.5 (t, 2H, J=7 Hz,

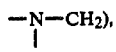

2.90 (t, 2H, J=7 Hz, CH$_2$), 1.30 (s, 9H, C—(CH$_3$)$_3$). Anal. (C$_{20}$H$_{25}$N$_2$O$_3$I) C, H, N.

EXAMPLE 27

Preparation of 1-Methyl-3-{N-[β-(4-hydroxyphenyl)ethyl]}carbamoyl-1,4-dihydropyridine (compound 27)

To an ice cold solution of 1.15 g (3 mmol) of compound 25 in 200 ml of decanted water, 1.5 g (18 mmol) sodium bicarbonate was added. While the mixture was bubbled with N$_2$ gas, 2.09 g (12 mmol) of sodium dithionite was gradually added to the mixture. The mixture was stirred under N$_2$ for 1 hr and then extracted twice, each with 100 ml of ethyl acetate. The combined extract was washed with water, dried over anhydrous Na$_2$SO$_4$ and distilled on rotovap. Yield, 0.38 g (50%) of yellowish semisolid which reduces alcoholic AgNO$_3$TS instantaneously. (PMR as expected).

EXAMPLE 28

Preparation of 1-Methyl-3-{N-[β-4-pivalyloxyphenyl)]}carbamoyl-1,4-dihydropyridine (compound 28)

To an ice cold mixture of 2.34 g (5 mmol) of compound 26, 200 ml of deaerated water and 100 ml of ethyl acetate, 1.63 g (20 mmol) sodium bicarbonate and 3.47 g (20 mmol) sodium dithionite were added while stirring the mixture. Stirring was continued under N$_2$ gas for 30 min. The ethyl acetate layer was separated and the aqueous layer was extracted with 100 ml of ethyl acetate. The combined ethyl acetate extract was washed with 100 ml cold deaerated water, dried over anhydrous Na$_2$SO$_4$ and evaporated on rotavap. The viscous, yellow residue was dissolved in 5 ml of acetone, filtered under N$_2$ gas through folded filter paper and distilled on rotavap. The solid residue was dried under vacuo over P$_2$O$_5$ in N$_2$ atmosphere. It reduced alcoholic AgNO$_3$ instantaneously. Yield, 1.06 g (62%). (PMR as expected.)

EXAMPLE 29

Preparation of 3,5-Pyridine dicarboxylic didecyl ester hydrochloride (compound 29)

3,5-Pyridine dicarboxylic acid (9.6 g, 0.06 moles) was converted to the diacid chloride by treatment with excess SOCl$_2$. The mixture was refluxed at 100° C. for 6 hrs. Excess SOCl$_2$ was distilled under reduced pressure and 25 ml of decyl alcohol dissolved in benzene were added. The solution was refluxed for 5 hrs after which benzene was distilled and the residue dissolved in ethyl ether. The organic phase was extracted with bicarbonate solution and later dried over Na$_2$SO$_4$. The ethyl ether solution was acidified with HCl (gas) and 24.2 g of compound 29 (95% yield, m.p. 80-90PC) were obtained. 1H (NMR) CDCl$_3$/d$_6$DMSO δ9.3 (3H, bs), 8.7 (1H, bs), 4.3 (4H, bT) and 1.4 (38H, bm) ppm.

EXAMPLE 30

Preparation of Didecyl 3,5-dicarboxylate-1-methyl pyridinium iodide (compound 30)

Compound 29 (10 g, 0.025 moles) was dissolved in an ethyl ether/bicarbonate solution. The organic phase was rinsed with water and dried over Na$_2$SO$_4$. The solvent was evaporated and the residue dissolved in acetone and an excess of methyl iodide added. The solution was refluxed for 8 hrs, after which the solvent was evaporated and ethyl ether added to the residue. A yellow solid was obtained which was filtered and rinsed with more ethyl ether. The solid was recrystallized from a minimum amount of ethyl acetate to yield 12.5 g (85%) m.p. 104°-105° C. Analytical data: Theory: C, 57.04; H, 8.21. Found: C, 57.18; H, 8.09. Spectrophotometric data in methanol: λ219 ε=2.7×10$^4$ 1/mol cm; λ277 ε=3.6×10$^3$ 1/mol cm.

EXAMPLE 31

(i) Oxidation by Hydrogen Peroxide

To 10 ml of 30% H$_2$O$_2$ was added 0.2 g of the dihydropyridine derivative (compounds 4, 5, 10 or 13). The mixture was stirred and samples were taken to check the UV spectrum. Complete oxidation to the corresponding quaternary salts was observed.

(ii) Oxidation by Silver Nitrate

To 5 ml of saturated methanolic AgNO$_3$ solution was added 1 ml of 5% methanolic solution of the dihydropyridine derivative. The mixture was shaken and left for 5 min for complete precipitation of silver, centrifuged and an aliquot was taken to check the UV spectrum. Complete oxidation to the quaternary salts was observed.

(iii) Calibration Curves

UV study of compounds 2-5, 9, 10, 12 and 13 revealed that they obey Beer's Law with good coefficients and at a wide range of dilution levels. The study was done at 350 nm for the dihydro derivatives and at 262 and 220 nm for all the quaternary and dihydro.

EXAMPLE 32

Kinetics of Oxidation of the Dihydro Derivatives

In Plasma: 0.2 ml of (6.25×10$^{-4}$M) freshly prepared solution of the dihydro derivative in methyl alcohol was diluted to 10 ml with 20% plasma (diluted with phosphate buffer pH 7.4). The solution was kept at 37° and UV spectrum was scanned from 400 nm to 300 nm every 10 min for 2 hrs against reference made by dilution of 0.2 ml methyl alcohol with 20% plasma to 10 ml.

In Whole Blood: In each of 5 tubes, 0.1 ml of 10×10$^{-4}$M methanolic solution of the freshly prepared dihydro derivative, was added 2 ml of fresh heparinized whole human blood and the tubes were kept at 37° in a water bath, at the end of the time period to be investigated, 8 ml of acetonitrile was added, shaken vigorously and centrifuged. The extension of the supernatant solution at 350 nm was measured. A reference sample was made by addition of 0.1 ml of methyl alcohol instead of the sample solution following the same procedure.

In Brain Homogenate: 2.0 g of rat brain tissue were homogenized in 10 ml of phosphate buffer, pH 7.4. The homogenate was centrifuged for 15 min at 3000 rpm, decanted, heated in a water bath at 50° for 5 min and then centrifuged again. The supernatant solution was diluted to 100 ml with phosphate buffer, pH 7.4.

Reference Sample: 0.2 ml of methyl alcohol was diluted to 10 ml with the brain homogenate solution, and the solution was used to record the base line on Cary 219 spectrophotometer and as a reference for the dihydro derivative sample solution.

Dihydro Derivative Sample Solutions: 0.2 ml of $6.25 \times 10^{-4}M$ methanolic solution of the freshly prepared dihydro derivative was diluted to 10 ml with the brain homogenate solution. The mixture was scanned at 37° from 400 nm to 300 nm every 10 min for 2 hrs on Cary 210 spectrophotometer.

In Liver Homogenate:
Liver Homogenate Solution: 5.0 g of rat liver tissue were homogenized in 50 ml of phosphate buffer, pH 7.4. The homogenate was centrifuged, decanted, heated in a water bath at 50° for 5 min and then centrifuged again. The supernatant homogenate was diluted to 250 ml with phosphate buffer, pH 7.4.

Reference Sample: 0.2 ml of methyl alcohol was diluted to 10 ml with the liver homogenate solution and the solution and the solution was used to record the base line on a Cary 219 spectrophotometer and as a reference for the dihydro derivative sample solution.

Dihydro Derivative Sample Solution: 0.2 ml of $6.25 \times 10^{-4}M$ solution of the freshly prepared dihydro derivative in methyl alcohol was diluted to 10 ml with liver homogenate solution. The mixture was scanned at 37° from 400 nm to 300 nm every 5 min for 1 hr.

TABLE II

Kinetics of Oxidation

| | Comp. | | | |
|---|---|---|---|---|
| | 1-Methyl-3-(N—β-phenethyl)carbamoyl-1,4-dihydropyridine (5) | | 1-Benzyl-3-(N—β-phenethyl)carbomyl-1,4-dihydropyridine (4) | |
| Medium | K sec$^{-1}$ | t½ m | K sec$^{-1}$ | t½ m |
| Plasma | $1.8 \times 10^{-4}$ n = 13  r = .998 | 64.2 | $7.4 \times 10^{-5}$ n = 12  r = .998 | 156.1 |
| Whole Blood | $8.4 = 10^{-4}$ n = 5  r = .952 | 13.7 | $4.7 \times 10^{-4}$ n = 5  r = .974 | 24.4 |
| Brain Homogenate | $4.1 \times 10^{-4}$ n = 8  r = .996 | 28.2 | $2.1 \times 10^{-4}$ n = 13  r = .999 | 55 |
| Liver Homogenate | $8.0 \times 10^{-4}$ n = 7  r = .999 | 14.4 | $7.5 \times 10^{-4}$ n = 5  r = .998 | 15.3 |

| | Compound 13 | | Compound 10 | |
|---|---|---|---|---|
| Brain Homogenate | $8.4 = 10^{-6}$ n = 6  r = .997 | 22.9 | $1.74 \times 10^{-5}$ n = 6  r = .993 | 11.1 h |
| Whole Blood | $4.9 \times 10^{-5}$ n = 5  r = .949 | 3.9 | $1.13 \times 10^{-4}$ n = 5  r = .972 | 1.7 h |

EXAMPLE 33

In Vivo Study on
1-Methyl-3-(N-β-phenethyl)carbamyl-1,4-dihydropyridine (compound 5)

A group of rats of average weight (about 350 g) was injected through the jugular with a solution of the freshly prepared dihydro derivative in DMSO (0.05 g/ml solution) in a dose level of 125 mg/kg animal body weight. After the appropriate time period, 1 ml of blood was withdrawn from the heart and the animal was perfused with 20 ml of saline solution. The animal was decapitated. The brains were weighed, kept in the refrigerator overnight and homogenized in 2 ml of water. Acetronitrile, 8 ml, was added and the mixture was homogenized again and then centrifuged. The amount of the quaternary was determined from the HPLC spectrum in relation to a recovery experiment made by adding a specific amount of the quaternary to a blank brain and hybrid in the same manner of homogenization and extraction.

| Brain Results: | | | |
|---|---|---|---|
| t | Normalized value amt in mg/weight lb in grams | t | Normalized value |
| 5 | .055 | 40 | .1132 |
| 5 | .0423 | 47 | .125 |
| 10 | .099 | 66 | 148 |
| 15 | .0553 | 90 | .1626 |
| 15 | .100 | 90 | .1294 |
| 20 | .0935 | 145 | .0949 |
| 21 | .0743 | 180 | .0838 |
| 25 | .101 | 185 | .1001 |
| 30 | .1242 | 210 | .0707 |
| 32 | .095 | 220 | .0753 |
| 33 | .0778 | | |

Blood Concentration: The blood withdrawn was left in the refrigerator overnight and 3 ml of saline was added and the mixture shaken, then 17 ml of acetonitrile was added and the mixture was shaken vigorously for 1 min and then centrifuged. The supernatant solution was injected directly into the HPLC. Results:

| t (m) | mg/ml |
|---|---|
| 25 | .0235 |
| 40 | .0117 |
| 21 | .0205 |
| 33 | .0058 |
| 5 | .0294 |
| 75 | .0058 |
| 40 | .0088 |
| 15 | .0235 |

EXAMPLE 34

Kinetics of Disappearance of the Quaternary From Brain Homogenate

A fresh perfused rat brain was homogenized in 20 ml of phosphate buffer, pH 7.4. A solution of 10.0 mg of 1-methyl-3-(N-β-phenethyl)carbamoyl pyridinium iodide in 2 ml aqueous methanol (1:1) was added and the thoroughly mixed mixture was kept at 37° C. in a waterbath. At each time period, 1 ml of the mixture was taken and shaken thoroughly with 8 ml of acetonitrile, centrifuged and injected to HPLC. The amount of the quaternary in the sample was determined in comparison with a sample taken at time 0. Linear regression of t against log C shows that $K=4.8 \times 10^{-5}$ sec$^{-1}$, t½=3.50 h (in vivo exp.) which was found to be $K=8.45 \times 10^{-5}$ sec$^{-1}$, t½=2.1 g h, r=0.957.

EXAMPLE 35

Studies on the Dopamine Derivative, Compound 22

Analytical Methods: A high pressure liquid chromatography (HPLC) method was developed for the studies of the degradation of the dihydropyridine derivative. The chromatographic analysis was performed on a component system consisting of a Waters Associates Model 6000A solvent delivery system, a Model U6K injector and a Model 440 dual channel absorbance detector operated at 254 and 280 nm. A 30 cm×3.9 mm (internal diameter) reverse phase μ-Bondapak $C_{18}$ column (Waters Associates), operated at ambient temperature, was used for all separations. The mobile phase used for the separation of the dihydropyridine derivative, its degradation products and oxidation products consisted of 0.005M solution of 1-heptane-sulfonic acid sodium salt (PIC B-7-Eastman Kodak) in $CH_3CN$; 0.01M aqueous dibasic ammonium phosphate (2.5:1). At a flow rate of 2.0 ml/min, compound 4 had a retention time of 5.1 min; compound 5, 11.8 min; compound 7, 1.7 min; compound 22, 3.1 min. A peak was always shown at a retention time of 2.2 min which is thought to be a mono-deacylated dihydropyridine derivative.

Determination of the Enzymatic Hydrolytic Cleavage and Rate of Oxidation of Compound 22

In Human Plasma: a. (using HPLC) The freshly collected plasma used was obtained at the Civitan Regional Blood Center, Inc. (Gainesville, Fla.) and contained about 80% plasma diluted with anticoagulant citrate phosphate destrose solution U.S.P. The plasma was stored in a refrigerator and used the next day. 100 μl of a freshly prepared 0.61M solution of compound 22 in methanol was added to 20 ml plasma, previously equilibrated to 37° in a water bath and mixed thoroughly to result in an initial concentration of $3.05 \times 10^{-3}$ moles/liter. One (1.0) ml samples of plasma were withdrawn from the text medium, added immediately to 5 ml of ice cold acetonitrile, shaken vigorously and placed in a freezer. When all samples had been collected, they were centrifuged and the supernatants were filtered through Whatman 1 filter paper and analyzed by HPLC.

b. (using a Cary 219 spectrophotometer) 100 μl of ($9.05 \times 10^{-4}$M) freshly prepared solution of the dihydropyridine derivative in methyl alcohol was diluted to 10 ml with 20% fresh plasma (diluted with phosphate buffer, pH 7.4). The mixture was kept at 37° and the UV spectrum was scanned at 400-300 nm every 20 min for 2 hrs. The reference was prepared by diluting 0.2 ml of methyl alcohol with 20% plasma to 10 ml.

In Human Blood: The freshly collected heparinized blood was obtained at the Civitan Regional Blood Center, Inc. (Gainesville, Fla.). The blood was stored in a refrigerator and used the next day. 100 μl of a freshly prepared 0.18M solution of compound 22 in methanol was added to 20 ml blood, previously equilibrated to 37° C. in a water bath and mixed thoroughly to result in an initial concentration of $9 \times 10^{-4}$ moles/liter. One ml samples of blood were withdrawn from the test medium every 5 min, added immediately to 5 ml of ice cold acetonitrile, shaken vigorously and placed in a freezer. When all samples had been collected they were centrifuged and the supernatants were filtered using Whatman 4 filter paper and analyzed by HPLC.

In Rat Brain Homogenate: The brain homogenate was prepared by the following method. Five Sprague-Dawley rats were killed by decapitation and the brains were removed, weighed (total weight 9.85 g) and homogenized in 49.3 ml of aqueous 0.11M phosphate buffer, pH 7.4. The homogenate was centrifuged and the supernatant was used for the test. 100 μl of 0.18M solution of compound 22 was mixed with 10 ml of the homogenate, previously equilibrated to 37° C. in a water bath, to result in initial concentration of $1.8 \times 10^{-3}$ moles/liter. Samples of 1.0 ml were withdrawn every 10 min from the test medium, added immediately to 5 ml of ice cold acetonitrile and placed in a freezer. When all samples had been collected, they were centrifuged. Each supernatant was filtered through two Whatman 1 filter papers and analyzed by HPLC.

In Rat Liver Homogenate: The liver homogenate was prepared by the following method. Three Sprague-Dawley rats were killed by decapitation and the livers were removed, weighed and homogenized by tissue homogenizer in 0.11M aqueous phosphate buffer, pH 7.4, to make 20% liver homogenate. The homogenate was centrifuged and the supernatant was used for the test. 100 l of 0.1M solution of compound 22 in methanol was mixed with 20 ml of the homogenate, previously equilibrated to 37° C. in a water bath, to result in an initial concentration of $9 \times 10^{-4}$ moles/liter. Samples of 1.0 ml were withdrawn every 5 min from the test medium, added immediately to 5 ml of ice cold acetonitrile, shaken vigorously and placed in a freezer. When all samples had been collected, they were centrifuged and each supernatant was filtered through Whatman 1 filter paper and analyzed by HPLC.

Rates of disappearance (overall oxidation and degradation of compound 22:

(i) in Plasma:
$R = 2.25 \times 10^{-4}$ sec$^{-1}$
$t_{\frac{1}{2}} = 51.3$ min
$r = 0.998$
$n = (3 \times 6)$ (ii) In 20% Brain Homogenate:
$R = 6.7 \times 10^{-4}$ sec$^{-1}$
$t_{\frac{1}{2}} = 17.2$ min
$r = 0.996$
$n = (3 \times 6)$ (iii) In Blood:
$R = 6.3 \times 10^{-4}$
$t_{\frac{1}{2}} = 18.2$ min
$r = 0.997$
$n = (3 \times 7)$ (iv) In Liver:
$R = 1.93 \times 10^{-3}$
$t_{\frac{1}{2}} = 5.9$ min
$r = 0.950$
$n = (3 \times 5)$ In the Examples next to follow, all melting points were taken on a Mel-Temp apparatus and are uncorrected. Elemental analysis was performed at Atlantic Microlabs, Inc., Atlanta, Ga. Infrared spectra were determined using a Beckman Acculab 1 double-beam recording spectrophotometer. NMR spectra were determined by means of Varian T60A or FX100 spectrometers. All chemical shifts reported are in δ units (ppm) relative to TMS. Ultraviolet absorbance spectra were determined using a Cary Model 210 spectrophotometer. HPLC analyses were performed on a Beckman 345 ternary liquid chromatograph with Model 112 solvent delivery systems Model 210 injector, Model 160 absorbance detector and Model 421 controller.

EXAMPLE 36

Preparation of Testosterone nicotinate (compound 31)

Thionyl chloride (2 ml) was added to 0.7 g (5.7 mmol) of nicotinic acid and the mixture was refluxed for 3 hrs. Excess thionyl chloride was distilled under vacuum. To the cold residue 10 ml of dry pyridine was added followed with 1.44 g (5.0 mmol) of testosterone. The mixture was heated while stirring over a boiling water bath for 3 hrs. Pyridine was distilled under vacuum and 5 ml of methanol was added to the oily residue. The mixture was cooled and the solid crystallized out was filtered and recrystallized from methanol/acetone mixture. Yield, 1.4 g (71%), m.p. 187°–188°.

EXAMPLE 37

Preparation of 17β-[(1-Methyl-3-pyridinium carbonyl)oxy]androst-4-en-3-one iodide (compound 32) (Testosterone-17-nicotinate N-methyl iodide To a solution of 1.0 g (2.5 mmol) of testosterone nicotinate (31) in 15 ml of acetone, 1 ml of methyl iodide was added and the mixture was refluxed overnight. The yellow solid separated was filtered, washed with acetone and crystallized from methanol/ether mix. m.p. 215°–220° (dec.), yield 1.25 g (92%). U.V. ($CH_3OH$) λ270 nm (shoulder) ε=4579; 240 nm (shoulder), ε=19375. NMR ($CDCl_3$) δ10.0–8.3 (ms, 4H, pyridinium protons), 5.73 (s, 1H, $C_4$ testosterone proton), 4.86 (s, 3H, +N—$CH_3$), 2.40–1.06 (ms, 26H, testosterone skelton protons). Analysis calculated for $C_{26}H_{34}INO_3$: C, 58.22; H, 6.40; N, 2.62. Found: C, 58.17; H, 6.48; N, 2.60.

EXAMPLE 38

Preparation of 17β-[(1,4-Dihydro-1-methyl-3-pyridinylcarbonyl)oxy]androst-4-en-3-one (compound 33)

To an ice cold solution of 1.1 g (2 mmol) of testosterone nicotinate-N-methyl iodide (2) in 150 ml of deaerated 10% aqueous methanol, 0.67 g (8 mmol) of sodium bicarbonate and 1.37 g (8 mmol) of sodium dithionite were added. The mixture was stirred for 20 minutes and the pale yellow solid separated was filtered, washed with water and dried over $P_2O_5$ under vacuum. Wt. 0.82 g (98%), m.p. 172°–175° ($CH_3OH$); UV ($CH_3OH$) λ356 nm, ε=9511; ir (KBr) 1700, 1660 $cm^{-1}$ (two C=O stretching). NMR ($d_6$-DMSO) δ6.90 (bs, 1H, $C_2$ dihydropyridine proton) 5.83–5.70 (m, 1H, $C_6$ dihydropyridine proton), 5.56 (s, 1H, $C_4$ testosterone proton), 4.7–4.33 (m, 1H, $C_5$ dihydropyridine proton), 3.26 (bs, 2H, $C_4$ dihydropyridine protons), 2.93 (s, 3H, N—$CH_3$), 2.5–0.83 (m, 26H, testosterone skelton protons with the angular methyl protons at 1.16 and 0.83). Analysis calculated for $C_{26}H_{35}NO_3$: C, 76.25; H, 8.61; N, 3.42. Found: C, 76.07; H, 8.65; N, 3.38.

EXAMPLE 39

Analytical Methods

A high pressure liquid chromatograph (HPLC) method was developed for the studies of the degradation of the quaternary (32) and dihydropyridine derivative (33). The chromatographic analysis was performed on a component Ternary system consisting of a Beckman Model 112 solvent delivery system, Model 210 injector and Model 160 absorbance detector operated at 254 nm. A 15 cm×4.6 mm (internal diameter), 5 μm particle site ultrasphere reverse phase $C_{18}$ column (Altex), operated at ambient temperature, was used for all separations. The mobile phase used for the separation of the dihydropyridine derivative, its degradation products and oxidation products consisted of 0.002M solution of 1-heptane-sulfonic acid sodium salt (PIC B-7 Eastman Kodak) in $CH_3CN$, 0.01M aqueous dibasic ammonium phosphate (7:3). At a flow rate of 2.0 ml/min, compound 32 had a retention time of 12 min and compound 33, 5 min. For the analysis of testosterone in the in vivo brain delivery studies, a solvent system consisted of 0.002M solution of PIC-7 in $CH_3CN$; 0.1M aqueous dibasic ammonium phosphate (1:1). At a flow rate of 2.0 ml/min testosterone had a retention of 3.3 min and compound 32 had a retention time of 36.5 min (very broad peak).

EXAMPLE 40

Chemical Oxidation Studies (i) By Silver Nitrate: 1 ml of 5% methanolic solution of the dihydropyridine compound 33 was added to 5 ml of saturated methanolid $AgNO_3$ solution. The mixture was shaken, left 10 minutes for complete oxidation, centrifuged and taken to check to UV spectrum.

(ii) By Hydrogen Peroxide: To a standardized solution of $H_2O_2$ (0.18M) contained in a UV cuvettes equilibrated at 37°, a solution of dihydropyridine compound 33 was added to the sample cuvette to make concentration at about $5\times10^{-6}$M. The mixture was thoroughly mixed and monitored for the disappearance of the dihydropyridine maximum at 356 nm using a Cary 210 dedicated to an Apple II microprocessor and using an enzyme kinetic software package.

(iii) By Diphenylpicrylhydrazyl Free Radical: To 2 ml of $9.3\times10^{-5}$M solution of 2,2-diphenyl-1-picrylhydrazyl free radical in acetonitrile, equilibrated at 26° C., 20 ml of $1.5\times10^{-2}$M solution of the dihydropyridine compound 33 in acetonitrile was added. The mixture was monitored at 515 nm against a reference cuvette containing the same mixture in exactly the same concentrations, but previously prepared and left for at least 10 minutes and used as reference for A∞. The instrument used was a Cary 210 dedicated to an Apple II microprocessor and using an enzyme kinetic software package.

EXAMPLE 41

Determination of In Vitro Rates of Oxidation of Compound 33 in Biological Media

In Human Plasma

The freshly collected plasma used was obtained at the Civitan Regional Blood Center, Inc. (Gainesville, Fla.) and contained about 80% plasma diluted with anticoagulant citrate phosphate dextrose solution U.S.P. The plasma was stored in a refrigerator and used the next day. 100 μl of a freshly prepared 0.024M solution of compound 33 in DMSO was added to 10 ml plasma, previously equilibrated to 37° in a water bath and mixed thoroughly to result in an initial concentration of $2.4\times10^{-4}$ moles/liter. One ml samples of plasma were withdrawn every 20 minutes from the test medium, added immediately to 5 ml of ice cold acetonitrile, shaken vigorously and placed in a freezer. When all samples had been collected, they were centrifuged and the supernatants were filtered through nitrocellulose membrane filters (Por. 45) and analyzed by HPLC.

In Human Blood

The freshly collected heparinized blood was obtained at the Civitan Regional Blood Center, Inc. (Gainesville, Fla.). The blood was stored in a refrigerator and used the next day. 100 μl of a freshly prepared 0.048M solution of compound 33 in DMSO was added to 20 ml blood, previously equilibrated to 37° C. in a water bath and mixed thorougly to result in an initial concentration of $2.4\times10^{-4}$ moles/liter. One ml samples of blood were withdrawn from the test medium every 10 minutes, added immediately to 5 ml of ice cold acetonitrile, shaken vigorously and placed in a freezer. When all samples had been collected, they were centrifuged and the supernatants were filtered using nitrocellulose membrane filters (Por. 45) and analyzed by HPLC.

In Rat Brain Homogenate

The brain homogenate was prepared by the following method. Five female Sprague-Dawley rats were killed by decapitation and the brains were removed, weighed (total weight 9.2 g) and homogenized in 36.8 ml of aqueous 0.11M phosphate buffer, pH 7.4. 100 µl of 0.024M solution of compound 33 in DMSO was mixed with 20 ml of the homogenate, previously equilibrated to 37° C. in a water bath to result in an initial concentration of $2.4 \times 10^{-4}$ moles/liter. Samples of 1.0 ml were withdrawn every 10 minutes from the test medium, added immediately to 5 ml of ice cold acetonitrile, shaken vigorously and placed in a freezer. When all samples had been collected, they were centrifuged and the supernatants were filtered through nitrocellulose membrane filter (Por. 0.45) and analyzed by HPLC.

EXAMPLE 42

In Vitro Determination of the Site-Specific Conversion of the Prodrug (32)

A fresh brain homogenate was prepared as above described. 100 µl of 0.017M solution of the quaternary compound 32 in methanol was mixed with 10 ml of the brain homogenate, previously equilibrated to 37° C. to result in an initial concentration of $1.7 \times 10^{-4}$M. Samples of 1.0 ml were withdrawn every 20 minutes from the test medium, added immediately to 5 ml of ice cold acetonitrile and placed in a freezer. When all samples had been collected they were centrifuged and the supernatant was filtered through nitrocellulose membrane filter (Por 0.45) and analyzed for the quaternary.

EXAMPLE 43

In Vivo Brain Delivery of Testosterone Following Administration of the Dihydro Compound 33

Female Sprague-Dawley rats of average wieght of 225±10 g were used. The rats were anaesthetized with IM injection of Innovar ® (0.13 ml/kg) and the external jugular was exposed. Compound 33 was injected intrajugularly in the form of 2.5% solution in DMSO at a dose of 40 mg/kg (equivalent to 52.3 mg quaternary (32) or 28.2 mg testosterone). The injection was given at a rate of 44.4 1/minute using a calibrated infusion pump. After appropriate time periods, 1 ml of blood was withdrawn from the heart and dropped immediately into a tared tube containing 5 ml acetonitrile which was later weighed to determine the weight of the blood taken. The animal was then perfused with 20 ml of saline solution, decapitated and the brain was removed. The weighed brain was homogenized with 1 ml of distilled water, 5 ml of acetonitrile was added and the mixture was rehomogenized thoroughly, centrifuged, filtered and then analyzed using the HPLC method. The tubes containing the blood were shaken vigorously, centrifuged, filtered and also analyzed using the HPLC method described at 0.05 sensitivity limit for determination of the quaternary (32) and at 0.001 sensitivity limit for determination of liberated testosterone. Quantitation was done using a recovery standard curve obtained by introducing a known amount of either compound 32 or testosterone in either brain homogenate or blood and then treated in the same manner of extraction and analysis.

EXAMPLE 44

In Vivo Brain Delivery of Testosterone Following its Administration

Female Sprague-Dawley rats with an average weight of 225±10 g were injected with testosterone at a dose level of 28.2 mg/kg following the same procedure previously described. Samples of brain and blood collected were analyzed for testosterone using HPLC.

EXAMPLE 45

In Vivo Brain Delivery of Quaternary 32 Following its Administration

Following the same procedure, female Sprague-Dawley rats were injected with the quaternary solution (0.81%) in DMSO at a dose level of 13.0 mg/kg (it was found to be toxic at higher doses). The brain samples collected were analyzed for presence of the quaternary (32) using HPLC.

EXAMPLE 46

Results of Experiments of Examples 40-45

Chemical Oxidation of the Dihydropyridine Derivative (i) By Silver Nitrate: It was observed that this dihydro compound 33 was more stable towards oxidation than the monophenethylamine type derivatives and the product was exclusively the quaternary.

(ii) By Hydrogen Peroxide: At low concentrations of the dihydro compound 33, $5 \times 10^{-6}$M compared to the high concentration of the peroxide (0.18M), the oxidation was of first order kinetics.

$k = 2.7 \pm 0.3 \times 10^{-3}$ sec$^{-1}$; $t_{\frac{1}{2}} = 3.98 \pm 0.7$ min; $r = 0.995$ At higher concentrations the dihydro compound was insoluble in $H_2O_2$.

(iii) By Diphenylpicrylhydrazyl (DPP) Free Radical. The reaction was carried out under pseudo first order conditions using excess of the dihydropyridine derivative. With the concentrations used, all runs gave good first order plots over 3 half lives with correlation coefficient better than 0.9998.

$k = 4.87 \pm 0.31 \times 10^{-2}$ sec$^{-1}$; $t_{\frac{1}{2}} = 14.1 \pm 0.6$ seconds Trials to determine the second order rate constant using different concentrations of DPP were unsuccessful.

(iv) In Vitro Oxidation in Biological Media:

| Medium | k | $t_{\frac{1}{2}}$ min | r | Note |
|---|---|---|---|---|
| 80% Plasma | $8.12 \times 10^{-5}$ | 142 | .959 | quat. 32 increase |
| 20% Brain homogenate | $1.72 \times 10^{-4}$ | 67 | .997 | quat. 32 increase |
| Whole blood | $1.74 \times 10^{-4}$ | 66 | .997 | quat. 32 increase and dihydro 33 decrease |

20% Liver homogenate, very irregular data
Hydrolysis of the quaternary 32 in brain homogenate: $3.6 \times 10^{-5}$; 5:16 h; 0.962

(v) In Vivo Administration of Compound 33 Against Testosterone

Figure 4:
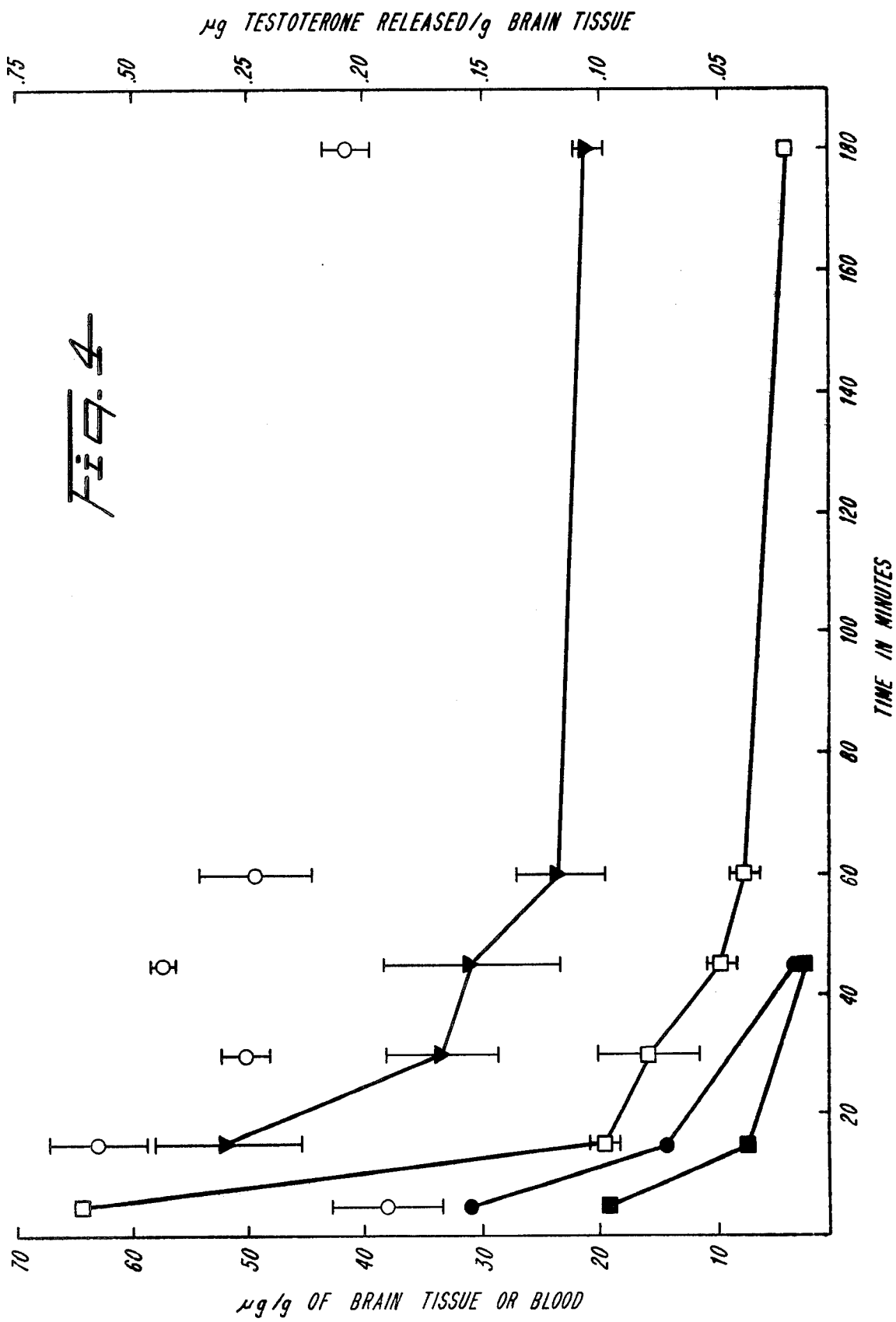

These results are shown in FIG. 4. Statistical analysis of the descending portions of the curves provides the following results:

(1) Rates of disappearance of the quaternary compound 32:

from brain=$2\times 10^{-3}$ min$^{-1}$; $t_{\frac{1}{2}}$=5.7 h; r=0.833
from blood=$1.27\times 10^{-2}$ min$^{-1}$; $t_{\frac{1}{2}}$=54 min; r=0.833

(2) Rate of disappearance of released testosterone following administration of dihydro compound (33)=$2.65\times 10^{-3}$ min$^{-1}$; $t_{\frac{1}{2}}$=4.4 h; r=0.768
(Results analyzed for up to 5 hrs, the data shown in FIG. 4 are for 3 hrs)

(3) Rate of disappearance of testosterone following administration of testosterone:

from brain=$5.5\times 10^{-2}$ min$^{-1}$; $t_{\frac{1}{2}}$=12.6 min; r=0.994
from blood=$4.74\times 10^{-2}$ min$^{-1}$; $t_{\frac{1}{2}}$=14.5 min; r=0.959

In said FIG. 4 are plotted concentrations, with standard errors against time, for testosterone-17-nicotinate-N-methyl cation, calculated as iodide, in brain (O) and in blood (□) and concentration of released testosterone in brain (▼), both following administration of the corresponding dihydropyridine compound 33. Also plotted are concentrations of testosterone in brain (●) and blood (■) following administration of testosterone, per se.

Accordingly, provided hereby are not only a generic method and novel class of pro-prodrugs for the specific and/or target enhanced delivery to the brain of a wide variety of drug species via the bidirectional transport of the drug species into and out of the brain employing dihydropyridine⇌pyridinium salt carrier redox systems, but also a system providing insight into the basic transport processes (both active and passive) of, and enzymatic activities in, the blood-brain barrier, as well as into the various processes specific to the function of the brain. And these as a result of the various syntheses, physical/chemical determinations on the individual drug/carrier redox combinations, in vitro kinetics of conversion of [D-DHC] to [D-QC]+ in various biological fluids, in vitro kinetics of the [D-QC]+→[D]+[QC]+ delivery mechanism, in vivo brain delivery determinations of [D-QC]+ via [D-DHC], systemic and brain pharmacokinetics of [D-QC]+ versus [D-DHC] and the release of [D], pharmacological studies, bidirectional transparent evaluations of the various drug species into and out of the brain, whole body distribution analyses, and the theoretical investigations of the energetic and electronic processes native to the topic redox systems, all as hereinabove characterized. Again, another very significant aspect of the bioreversible redox delivery system according to this invention is the toxicity implication, for significantly reduced is systemic toxicity by accelerating the elimination of the drug/quaternary carrier system. And even central toxicity is reduced by providing for low level, sustained release of the active drug species in the brain. Low toxicity is provided both as regards the quaternary carrier and in combination with the drug.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:
1. A compound having the formula

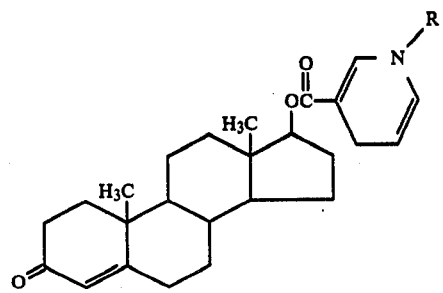

wherein R is lower alkyl or benzyl.

2. The compound as defined by claim 1, wherein R is methyl.

3. A pyridinium salt, the cation of which has the formula

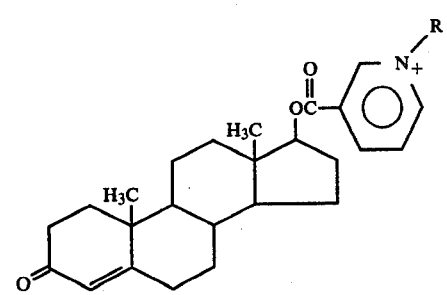

wherein R is lower alkyl or benzyl.

4. A salt as defined by claim 3, wherein R is methyl.

5. A method of site-specifically/sustainedly delivering testosterone to the brain, said method comprising administering to an animal in need of such treatment a quantity of a compound as claimed in claim 1 sufficient to release a pharmacologically effective amount of testosterone to the brain.

6. A pharmaceutical composition of matter comprising a compound as claimed in claim 1 and a pharmaceutically acceptable carrier therefor.

7. A pharmaceutical composition of matter, in unit dosage form, for use in delivering a pharmacologically effective amount of testosterone to the brain, said composition comprising:

(i) an amount of a compound as claimed in claim 1 sufficient to release a pharmacologically effective amount of testosterone to the brain; and (ii) a pharmaceutically acceptable carrier therefor.

8. A compound adapted for the site-specific/sustained delivery of a centrally acting drug species to the brain, said compound having the formula

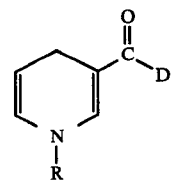

wherein R is lower alkyl or benzyl and D is the residue of the drug phenethylamine, amphetamine, dextroamphetamine, levamphetamine or phentermine, said residue being characterized by the absence of a hydrogen atom from the —NH$_2$ functional group in said drug.

9. A compound as defined by claim 8, wherein R is methyl.

10. A compound as defined by claim 8, wherein D is the residue of phenethylamine.

11. The compound as defined by claim 10, wherein R is methyl.

12. A compound as defined by claim 8, wherein D is the residue of amphetamine.

13. A compound as defined by claim 8, wherein D is the residue of dextroamphetamine.

14. A compound as defined by claim 8, wherein D is the residue of levamphetamine.

15. A compound as defined by claim 8, wherein D is the residue of phentermine.

16. A pyridinium salt, the cation of which has the formula

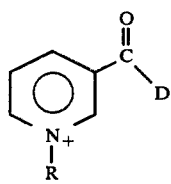

wherein R is lower alkyl or benzyl and D is the residue of the drug phenethylamine, amphetamine, dextroamphetamine, levamphetamine or phentermine, said residue being characterized by the absence of a hydrogen atom from the —NH$_2$ functional group in said drug.

17. A salt as defined in claim 16, wherein R is methyl.

18. A salt as defined by claim 16, wherein D is the residue of phenethylamine.

19. A salt as defined by claim 16, wherein D is the residue of amphetamine.

20. A salt as defined by claim 16, wherein D is the residue of dextroamphetamine.

21. A salt as defined by claim 16, wherein D is the residue of levamphetamine.

22. A salt as defined by claim 16, wherein D is the residue of phentermine.

23. A method for site-specifically/sustainedly delivering phenethylamine, amphetamine, dextroamphetamine, levamphetamine or phentermine to the brain, said method comprising administering to an animal in need of such treatment a quantity of a compound as claimed in claim 8 sufficient to release a pharmacologically effective amount of phenethylamine, amphetamine, dextroamphetamine, levamphetamine or phentermine, respectively, to the brain.

24. A pharmaceutical composition of matter comprising a compound as claimed in claim 8 and a pharmaceutically acceptable carrier therefor.

25. A pharmaceutical composition of matter, in unit dosage form, for use in delivering a pharmacologically effective amount of phenethylamine, amphetamine, dextroamphetamine, levamphetamine or phentermine to the brain, said composition comprising:

(i) an amount of a compound as claimed in claim 8 sufficient to release a pharmacologically effective amount of phenethylamine, amphetamine, dextroamphetamine, levamphetamine or phentermine, respectively, to the brain; and (ii) a pharmaceutically acceptable carrier therefor.

* * * * *

UNITED STATES PATENT AND TRADEMARK OFFICE
CERTIFICATE OF CORRECTION

PATENT NO. : 4,479,932
DATED : October 30, 1984
INVENTOR(S) : NICHOLAS S. BODOR

It is certified that error appears in the above—identified patent and that said Letters Patent is hereby corrected as shown below:

Column 42, lines 52, 53, 54 (Claim 8): Delete "adapted for the site-specific/sustained delivery of a centrally acting drug species to the brain, said compound"

Signed and Sealed this

Second Day of April 1985

[SEAL]

Attest:

DONALD J. QUIGG

Attesting Officer     Acting Commissioner of Patents and Trademarks